(12) United States Patent
Chanduszko et al.

(10) Patent No.: US 8,062,327 B2
(45) Date of Patent: Nov. 22, 2011

(54) EMBOLUS BLOOD CLOT FILTER AND DELIVERY SYSTEM

(75) Inventors: Andrzej J. Chanduszko, Chandler, AZ (US); David M. Graves, Mesa, AZ (US)

(73) Assignee: C. R. Bard, Inc., Murray Hill, NJ (US)

( * ) Notice: Subject to any disclaimer, the term of this patent is extended or adjusted under 35 U.S.C. 154(b) by 430 days.

(21) Appl. No.: 11/997,832

(22) PCT Filed: May 9, 2006

(86) PCT No.: PCT/US2006/017890
§ 371 (c)(1),
(2), (4) Date: Aug. 20, 2008

(87) PCT Pub. No.: WO2007/021340
PCT Pub. Date: Feb. 22, 2007

(65) Prior Publication Data
US 2009/0131970 A1    May 21, 2009

Related U.S. Application Data

(60) Provisional application No. 60/706,596, filed on Aug. 9, 2005.

(51) Int. Cl.
*A61F 2/01* (2006.01)
(52) U.S. Cl. ...................................................... 606/200
(58) Field of Classification Search .................. 606/108, 606/191, 194, 198, 200; 604/104–107, 164.01, 604/164.1, 164.11, 165.01, 165.02; 623/901–903; 128/830, 831, 833, 840
See application file for complete search history.

(56) References Cited

U.S. PATENT DOCUMENTS

| | | | |
|---|---|---|---|
| 2,767,703 A | 10/1956 | Nieburgs | |
| 3,472,230 A | 10/1969 | Fogarty | |
| 3,540,431 A | 11/1970 | Mobin-Uddia | |
| 3,579,798 A | 5/1971 | Henderson | |
| 3,620,212 A | 11/1971 | Fannon, Jr. et al. | |
| 3,952,747 A * | 4/1976 | Kimmell, Jr. | 128/899 |
| 4,198,960 A | 4/1980 | Utsugi et al. | |
| 4,425,908 A * | 1/1984 | Simon | 128/899 |
| 4,494,531 A | 1/1985 | Gianturco | |
| 4,586,501 A | 5/1986 | Claracq et al. | |
| 4,611,594 A | 9/1986 | Grayhack et al. | |
| 4,619,246 A | 10/1986 | Molgaard-Nielsen et al. | |
| 4,643,184 A * | 2/1987 | Mobin-Uddin | 606/200 |
| 4,655,219 A | 4/1987 | Petruzzi | |

(Continued)

FOREIGN PATENT DOCUMENTS
DE        3633527 A1    4/1988
(Continued)

OTHER PUBLICATIONS
International Search Report for PCT/US06/17890.
(Continued)

*Primary Examiner* — Elizabeth Houston
(74) *Attorney, Agent, or Firm* — Rutan & Tucker, LLP

(57) ABSTRACT

A blood filter delivery system for delivering a filter into a vein includes an introducer and a push rod with a spline member disposed along the push rod. The spline member has a main body, first and second boss portions spaced apart along the longitudinal axis to provide a gap for retaining anchor member of the filter during delivery via the introducer.

33 Claims, 13 Drawing Sheets

U.S. PATENT DOCUMENTS

| | | |
|---|---|---|
| 4,665,906 A | 5/1987 | Jervis |
| 4,680,573 A | 7/1987 | Ciordinik et al. |
| 4,688,553 A | 8/1987 | Metals et al. |
| 4,727,873 A | 3/1988 | Mobin-Uddin |
| 4,781,177 A | 11/1988 | Lebigot et al. |
| 4,793,348 A | 12/1988 | Palmaz |
| 4,817,600 A | 4/1989 | Herms et al. |
| 4,832,055 A * | 5/1989 | Palestrant .................... 128/899 |
| 4,957,501 A | 9/1990 | Lahille et al. |
| 4,969,891 A | 11/1990 | Gewertz |
| 4,990,151 A | 2/1991 | Wallsten |
| 4,990,156 A | 2/1991 | Lefebvre et al. |
| 5,059,205 A | 10/1991 | El-Nounou et al. |
| 5,067,957 A | 11/1991 | Jervis |
| 5,074,867 A | 12/1991 | Wilk |
| 5,098,440 A | 3/1992 | Hillstead |
| 5,108,418 A | 4/1992 | Lefebvre et al. |
| 5,120,308 A | 6/1992 | Hess |
| 5,133,733 A | 7/1992 | Rasmussen et al. |
| 5,147,378 A | 9/1992 | Markham |
| 5,147,379 A | 9/1992 | Sabbaghian et al. |
| 5,152,777 A | 10/1992 | Goldberg et al. |
| 5,190,546 A | 3/1993 | Jervis |
| 5,219,358 A | 6/1993 | Bendel et al. |
| 5,242,462 A | 9/1993 | El-Nounou et al. |
| 5,324,304 A * | 6/1994 | Rasmussen .................... 606/200 |
| 5,329,942 A | 7/1994 | Gunther et al. |
| 5,350,398 A | 9/1994 | Pavcnik et al. |
| 5,370,657 A | 12/1994 | Irie |
| 5,375,612 A | 12/1994 | Cottenceau et al. |
| 5,383,887 A | 1/1995 | Nadal et al. |
| 5,413,586 A | 5/1995 | Dibie et al. |
| 5,423,851 A | 6/1995 | Samuels |
| 5,464,408 A | 11/1995 | Duc |
| 5,531,788 A | 7/1996 | Dibie et al. |
| 5,545,210 A | 8/1996 | Hess et al. |
| 5,549,626 A | 8/1996 | Miller et al. |
| 5,554,181 A | 9/1996 | Das |
| 5,597,378 A | 1/1997 | Jervis |
| 5,601,595 A | 2/1997 | Smith |
| 5,626,605 A | 5/1997 | Irie et al. |
| 5,630,822 A | 5/1997 | Hermann et al. |
| 5,634,942 A | 6/1997 | Chevillon et al. |
| 5,649,906 A | 7/1997 | Gory et al. |
| 5,669,933 A | 9/1997 | Simon et al. |
| 5,683,411 A | 11/1997 | Kavteladze et al. |
| 5,695,518 A | 12/1997 | Laerum et al. |
| 5,704,910 A | 1/1998 | Humes |
| 5,709,704 A | 1/1998 | Nott et al. |
| 5,720,764 A * | 2/1998 | Naderlinger .................... 606/200 |
| 5,746,767 A | 5/1998 | Smith |
| 5,775,790 A | 7/1998 | Ohtake |
| 5,776,162 A | 7/1998 | Kleshinski |
| 5,776,181 A | 7/1998 | Lee et al. |
| 5,800,457 A | 9/1998 | Gelbfish |
| 5,836,968 A | 11/1998 | Simon et al. |
| 5,836,969 A | 11/1998 | Kim et al. |
| 5,853,420 A | 12/1998 | Chevillon et al. |
| 5,893,869 A | 4/1999 | Barnhart et al. |
| 5,911,704 A | 6/1999 | Humes |
| 5,919,224 A | 7/1999 | Thompson et al. |
| 5,928,261 A | 7/1999 | Ruiz |
| 5,944,728 A | 8/1999 | Bates |
| 5,954,741 A | 9/1999 | Fox et al. |
| 5,984,947 A | 11/1999 | Smith |
| 5,989,266 A | 11/1999 | Foster |
| 6,007,558 A | 12/1999 | Ravenscroft et al. |
| 6,013,093 A | 1/2000 | Nott et al. |
| 6,059,825 A | 5/2000 | Hobbs et al. |
| 6,080,178 A | 6/2000 | Meglin |
| 6,099,534 A | 8/2000 | Bates et al. |
| 6,126,673 A | 10/2000 | Kim et al. |
| 6,146,404 A | 11/2000 | Kim et al. |
| 6,156,055 A | 12/2000 | Ravenscroft |
| 6,193,739 B1 | 2/2001 | Chevillon et al. |
| 6,193,748 B1 | 2/2001 | Thompson et al. |
| 6,214,025 B1 | 4/2001 | Thistle et al. |
| 6,217,600 B1 | 4/2001 | DiMatteo |
| 6,231,581 B1 | 5/2001 | Shank et al. |
| 6,231,589 B1 * | 5/2001 | Wessman et al. ............. 606/200 |
| 6,241,738 B1 | 6/2001 | Dereume |
| 6,241,746 B1 | 6/2001 | Bosma et al. |
| 6,245,012 B1 | 6/2001 | Kleshinski |
| 6,251,122 B1 | 6/2001 | Tsukernik |
| 6,258,026 B1 | 7/2001 | Ravenscroft et al. |
| 6,264,664 B1 | 7/2001 | Avellanet |
| 6,267,776 B1 | 7/2001 | O'Connell |
| 6,267,777 B1 | 7/2001 | Bosma et al. |
| 6,273,900 B1 | 8/2001 | Nott et al. |
| 6,273,901 B1 | 8/2001 | Whitcher et al. |
| 6,280,451 B1 | 8/2001 | Bates et al. |
| 6,280,459 B1 | 8/2001 | Doble |
| 6,282,222 B1 | 8/2001 | Wieser et al. |
| 6,287,332 B1 | 9/2001 | Bolz et al. |
| 6,383,193 B1 * | 5/2002 | Cathcart et al. ................ 606/108 |
| 6,383,206 B1 | 5/2002 | Gillick |
| 6,391,045 B1 | 5/2002 | Kim et al. |
| 6,436,120 B1 | 8/2002 | Meglin |
| 6,436,121 B1 | 8/2002 | Blom |
| 6,443,972 B1 | 9/2002 | Bosma et al. |
| 6,447,530 B1 | 9/2002 | Ostrovsky et al. |
| 6,468,290 B1 | 10/2002 | Weldon et al. |
| 6,485,502 B2 | 11/2002 | Don Michael et al. |
| 6,497,709 B1 | 12/2002 | Heath |
| 6,506,205 B2 | 1/2003 | Goldberg et al. |
| 6,517,559 B1 | 2/2003 | O'Connell |
| 6,517,573 B1 | 2/2003 | Pollock et al. |
| 6,540,767 B1 | 4/2003 | Walak et al. |
| 6,551,340 B1 | 4/2003 | Konya et al. |
| 6,558,406 B2 | 5/2003 | Okada et al. |
| 6,569,183 B1 | 5/2003 | Kim et al. |
| 6,572,605 B1 | 6/2003 | Humes |
| 6,582,447 B1 | 6/2003 | Patel et al. |
| 6,589,266 B2 | 7/2003 | Whitcher et al. |
| 6,620,183 B2 | 9/2003 | DiMatteo |
| 6,623,506 B2 | 9/2003 | McGuckin, Jr. et al. |
| 6,645,224 B2 | 11/2003 | Gilson et al. |
| 6,652,558 B2 | 11/2003 | Patel et al. |
| 6,685,738 B2 | 2/2004 | Chouinard et al. |
| 6,702,834 B1 | 3/2004 | Boylan et al. |
| 6,706,054 B2 | 3/2004 | Wessman et al. |
| 6,843,798 B2 | 1/2005 | Kusleika et al. |
| 6,989,021 B2 * | 1/2006 | Bosma et al. .................. 606/200 |
| 7,314,477 B1 * | 1/2008 | Ravenscroft et al. .......... 606/200 |
| 7,338,512 B2 | 3/2008 | McGuckin, Jr. et al. |
| 7,544,202 B2 | 6/2009 | Cartier et al. |
| 7,625,390 B2 | 12/2009 | Hendriksen et al. |
| 7,699,867 B2 | 4/2010 | Hendriksen et al. |
| 7,704,267 B2 * | 4/2010 | Tessmer ........................ 606/200 |
| 2001/0000799 A1 | 5/2001 | Wessman et al. |
| 2002/0032461 A1 | 3/2002 | Marshall |
| 2002/0138097 A1 | 9/2002 | Ostrovsky et al. |
| 2002/0193828 A1 | 12/2002 | Griffin et al. |
| 2003/0004540 A1 | 1/2003 | Linder et al. |
| 2003/0004541 A1 | 1/2003 | Linder et al. |
| 2003/0004946 A1 | 1/2003 | VanDenAvond et al. |
| 2003/0055812 A1 | 3/2003 | Williams et al. |
| 2003/0114735 A1 | 6/2003 | Silver et al. |
| 2003/0130680 A1 | 7/2003 | Russell |
| 2003/0176888 A1 | 9/2003 | O'Connell |
| 2003/0208227 A1 | 11/2003 | Thomas |
| 2004/0073252 A1 | 4/2004 | Goldberg et al. |
| 2004/0082966 A1 | 4/2004 | WasDyke |
| 2004/0087999 A1 | 5/2004 | Bosma et al. |
| 2004/0088000 A1 | 5/2004 | Muller |
| 2004/0088001 A1 | 5/2004 | Bosma et al. |
| 2004/0088002 A1 | 5/2004 | Boyle et al. |
| 2004/0093015 A1 | 5/2004 | Ogle |
| 2004/0116959 A1 | 6/2004 | McGuckin et al. |
| 2004/0138693 A1 | 7/2004 | Eskuri et al. |
| 2004/0153110 A1 | 8/2004 | Kurz et al. |
| 2004/0153118 A1 | 8/2004 | Clubb et al. |
| 2004/0153119 A1 | 8/2004 | Kusleika et al. |
| 2004/0158274 A1 | 8/2004 | WasDyke |
| 2004/0167568 A1 | 8/2004 | Boyle et al. |
| 2004/0176672 A1 | 9/2004 | Silver et al. |
| 2004/0193209 A1 | 9/2004 | Pavcnik et al. |

| | | | |
|---|---|---|---|
| 2004/0220611 A1 | 11/2004 | Ogle | |
| 2004/0230220 A1 | 11/2004 | Osborne | |
| 2005/0021152 A1 | 1/2005 | Ogle et al. | |
| 2005/0055045 A1 | 3/2005 | DeVries et al. | |
| 2005/0055046 A1 | 3/2005 | McGuckin et al. | |
| 2005/0080449 A1* | 4/2005 | Mulder | 606/200 |
| 2005/0085847 A1 | 4/2005 | Galdonik et al. | |
| 2006/0106417 A1* | 5/2006 | Tessmer et al. | 606/200 |
| 2007/0112373 A1 | 5/2007 | Carr et al. | |
| 2007/0167974 A1 | 7/2007 | Cully et al. | |
| 2007/0198050 A1 | 8/2007 | Ravenscroft et al. | |
| 2008/0039891 A1 | 2/2008 | McGuckin et al. | |
| 2009/0318951 A1 | 12/2009 | Kashkarov et al. | |

FOREIGN PATENT DOCUMENTS

| | | |
|---|---|---|
| EP | 0145166 A2 | 6/1985 |
| EP | 0188927 A2 | 7/1986 |
| FR | 2567405 A1 | 1/1986 |
| FR | 2718950 A1 | 10/1995 |
| SV | 07A000025 | 4/1997 |
| WO | 9509567 A1 | 4/1995 |
| WO | 9612448 A1 | 5/1996 |
| WO | 9617634 A2 | 6/1996 |
| WO | 9802203 A1 | 1/1998 |
| WO | 9823322 A1 | 6/1998 |
| WO | 9925252 A1 | 5/1999 |
| WO | 0012011 A1 | 3/2000 |
| WO | 0018467 A1 | 4/2000 |
| WO | 0056390 A1 | 9/2000 |
| WO | 0076422 A1 | 12/2000 |
| WO | 0204060 A1 | 1/2002 |
| WO | 2004098459 A1 | 11/2004 |
| WO | 2004098460 A1 | 11/2004 |
| WO | 2005072645 A1 | 8/2005 |
| WO | 2005102437 A2 | 11/2005 |
| WO | 2005102439 A2 | 11/2005 |
| WO | 2006036457 A2 | 4/2006 |
| WO | 2006124405 A2 | 11/2006 |
| WO | 2007100619 A2 | 9/2007 |
| WO | 2007106378 A2 | 9/2007 |

OTHER PUBLICATIONS

C.R. Bard Simon Nitinol Filter: For Use in the Vena Cava: Instructions for Use (1995, 1997).
Cook "Bird's Nest" Vena Cava Filter, Cook Incorporated, a Cook Group Company, Nov. 1982.
Cook, "Gunther Tulip Vena Cava Mreye.TM. Filter" Sales Brochure (2001).
Cragg et al., "Nonsurgical Placement of Arterial Endoprostheses: A New Technique Using Nitinol Wire" Radiology 147:261-263 (Apr. 1983).
Cynamon et al., "Percutaneous Removal of a Titanium Greenfield Filter" AJR 159:777-778 (Oct. 1992).
Dotter et al., "Transluminal Expandable Nitinol Coil Stent Grafting: Preliminary Report" Radiology 147:259-260 (Apr. 1983).
Engmann and Asch, "Clinical Experience with the Antecubital Simon Nitinol IVC Filter" JVIR 9:774-778 (1998).
Epstein et al., "Experience with the Amplatz Retrievable Vena Cava Filter" Radiology 175:105-110 (1989).
Greenfield et al., "Results of a Multicenter Study of the Modified Hook—Titanium Greenfield Filter" Journal of Vascular Surgery 14:253-257 (Sep. 1991).
Hansen, "Metals that Remember", Science 81, Jun., pp. 44-47.
Kim et al., "Insertion of the Simon Nitinol Caval Filter: Value of the Antecubital Vein Approach" AJR 157:521-522 (Sep. 1991).

Kim et al., "Perforation of the Inferior Vena Cava with Aortic and Vetebral Penetration by a Suprarenal Greenfield Filter" Radiology 172:721-723 (1989).
Kim et al., "The Simon Nitinol Filter: Evaluation by MR and Ultrasound" Angiology 43:541-548 (Jul. 1992).
Kim et al., "Vena Cava Filter Placement Via the External Jugular Vein" AJR 155:898-899 (Oct. 1990).
Malden et al., "Transvenous Retreival of Misplaced Stainless Steel Greenfield Filters" JVIR 3:703-708 (1992).
McCowan et al., "Complications of the Nitinol Vena Cava Filter" JVIR 3:401-408 (1992).
Millward, "Temporary and Retrievable Inferior Vena Cava Filters: Current Status" JVIR 9:381-387 (1998).
Nakagawa et al., "A Retrievable Nitinol Vena Cava Filter: Experimental and Initial Clinical Results" JVIR 5:507-512 (1994).
Neuerburg et al., "New Retrievable Percutaneous Vena Cava Filter: Experimental In Vitro and In Vivo Evaluation" Cardiovasc. Intervent. Radiol. 16:224-229 (1993).
Palastrant et al., "Comparative in Vitro Evaluation of the Nitinol Inferior Vena Cava Filter" Radiology 145:351-355 (Nov. 1982).
PCT/US1999/020883 filed Sep. 23, 1999 Search Report dated Jan. 20, 2000.
PCT/US2006/017890 filed May 9, 2006 Preliminary Report on Patentability dated Feb. 12, 2008.
PCT/US2006/017890 filed May 9, 2006 Written Opinion dated Nov. 2, 2006.
Prince et al., "Local Intravascular Effects of the Nitinol Wire Blood Clot Filter" Investigative Radiology 23:294-390 (Apr. 1988).
Prince et al., "The Diameter of the Inferior Vena Cava and Its Implications for the Use of Vena Cava Filters" Radiology 149:687-689 (1983).
Putnam et al., "Placement of Bilateral Simon Nitinol Filters for an Inferior Vena Cava Duplication through a Single Groin Access" JVIR 10:431-433 (1999).
Qian et al., "In Vitro and In Vivo Experimental Evaluation of a New Vena Cava Filter" JVIR 5:513-518 (1994).
Salamipour et al., "Percutaneous Transfemoral Retrieval of a Partially Deployed Simon-Nitinol Filter Misplaced into the Ascending Lumbar Vein" JVIR 7:917-919 (1996).
Sequeira et al., "A Safe Technique for Introduction of the Kimray-Greenfield Filter" Radiology 133:799-800 (Dec. 1979).
Siegel and Robertson, "Percutaneous Tranfemoral Retrieval of a Free-Floating Titanium Greenfield Filter with an Amplatz Goose Neck Snare" JVIR 4:565-568 (1993).
Simon et al., "A Vena Cava Filter Using Thermal Shape Memory Alloy", Radiology, vol. 125, No. 1, Oct. 1977, pp. 89-94.
Simon et al., "Simon Nitinol Inferior Vena Cava Filter: Initial Clinical Experience" Radiology 172:99-103 (1989).
Simon et al., "Transvenous Devices for the Management of Pulmonary Embolism", CardioVascular and Interventional Radiology, 3:308-313, 1980, pp. 112-120.
Simon, "Vena Cava Filters: Prevalent Misconceptions" JVIR 10:1021-1024 (1999).
U.S. Appl. No. 11/150,661, filed Jun. 10, 2005 Final Office Action dated May 27, 2010.
U.S. Appl. No. 11/150,661, filed Jun. 10, 2005 Non-Final Office Action dated Nov. 5, 2009.
Vesley et al., "Preliminary Investigation of the Irie Inferior Vena Cava Filter" JVIR 7:529-535 (1996).
Zwaan et al., "Clinical Experience with Temporary Vena Cava Filters" JVIR 9:594-601 (1998).

* cited by examiner

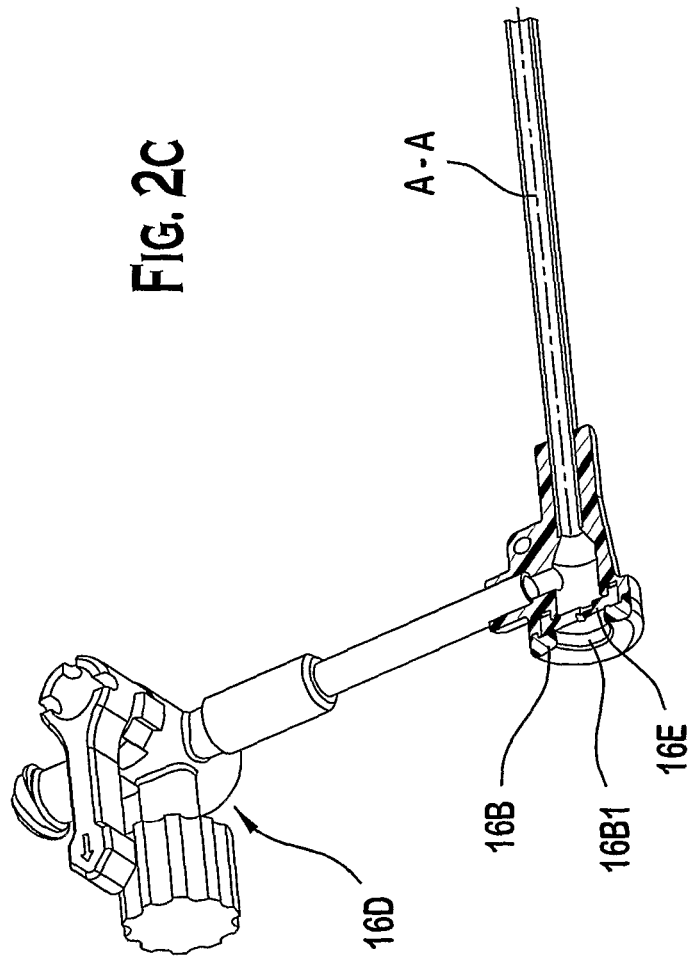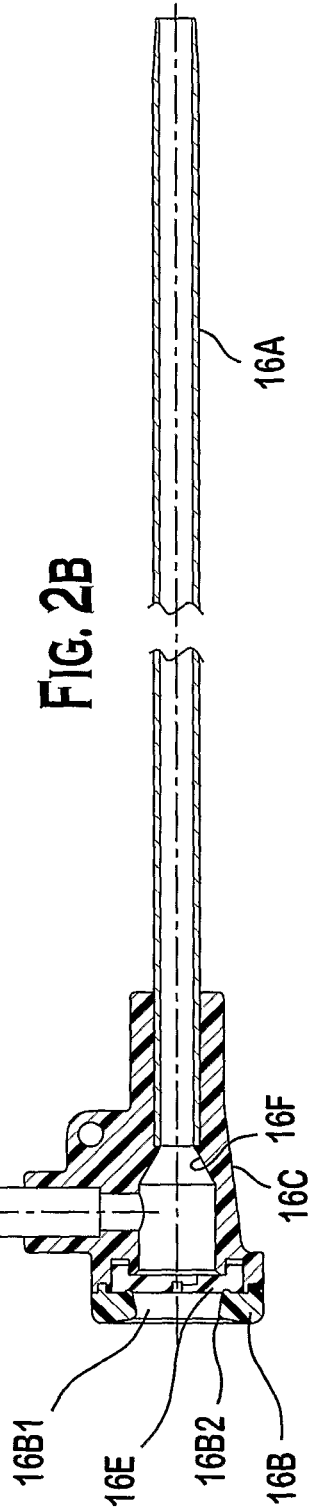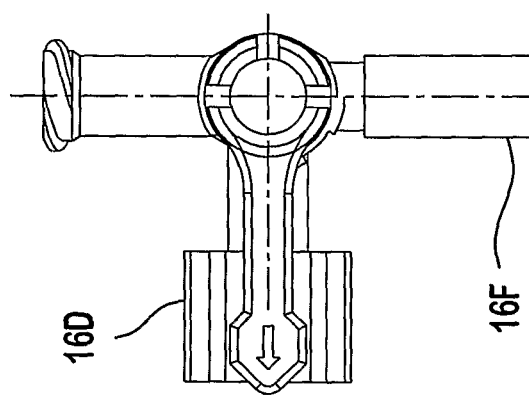

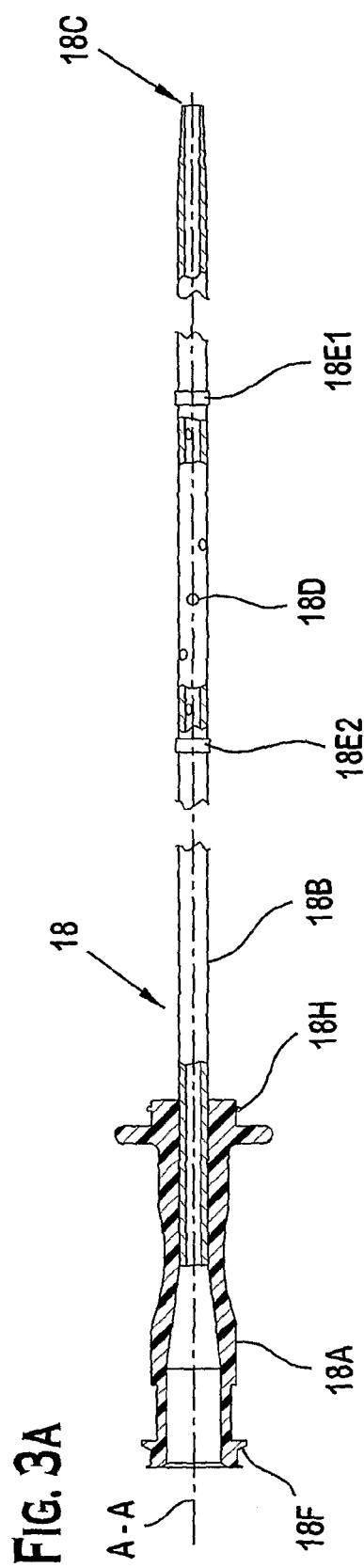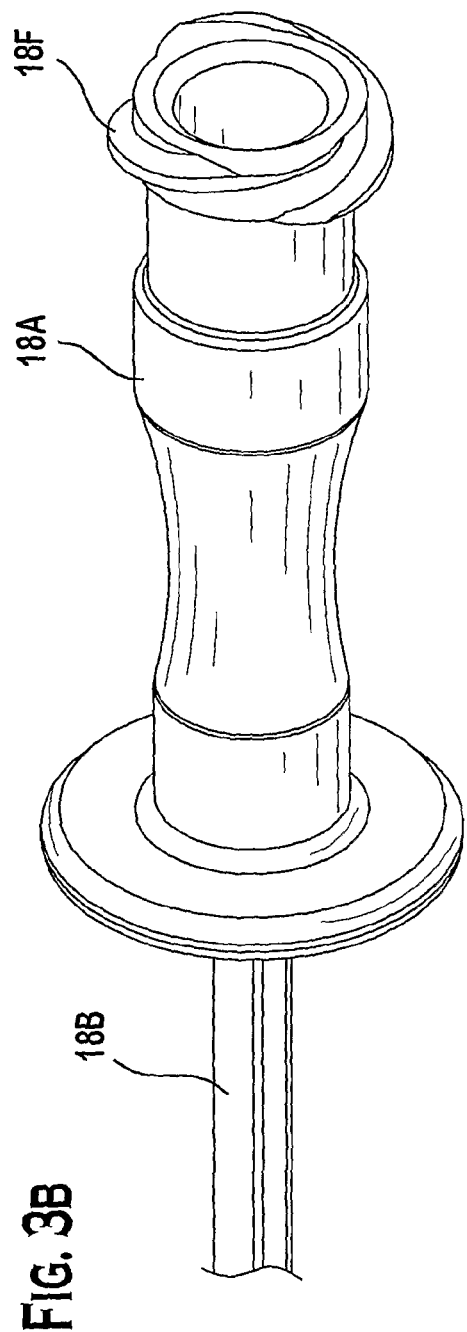

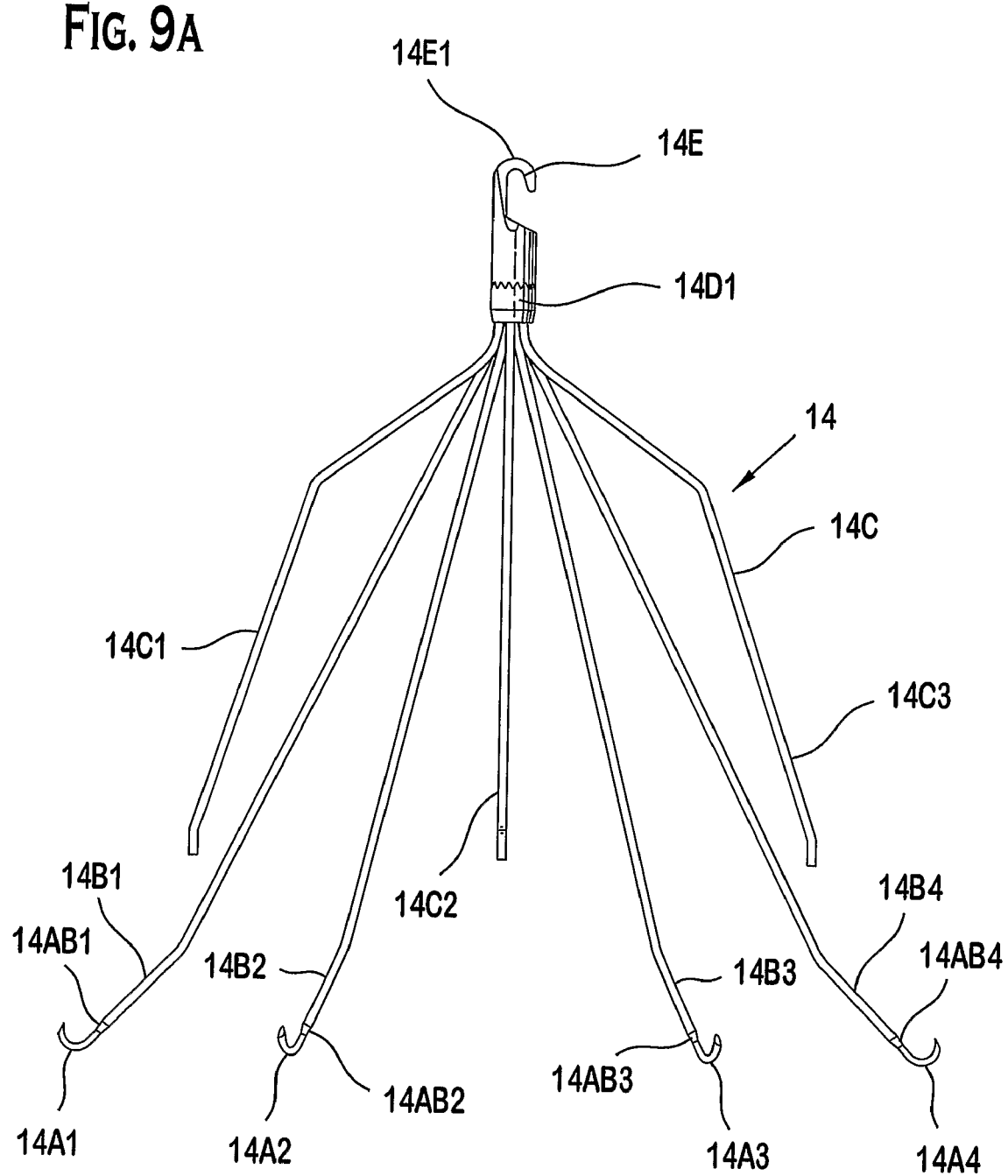

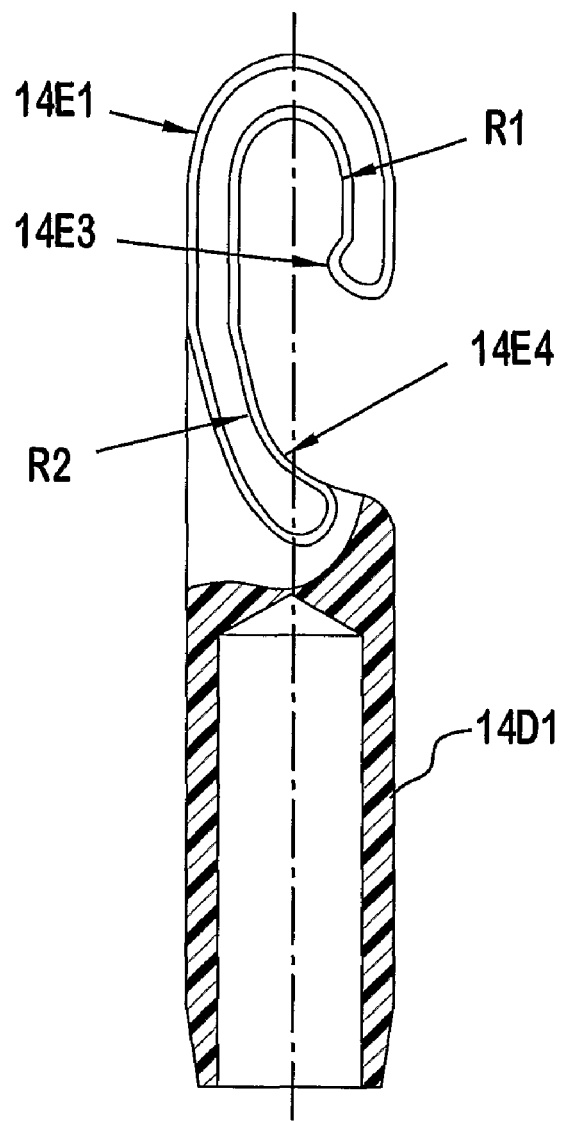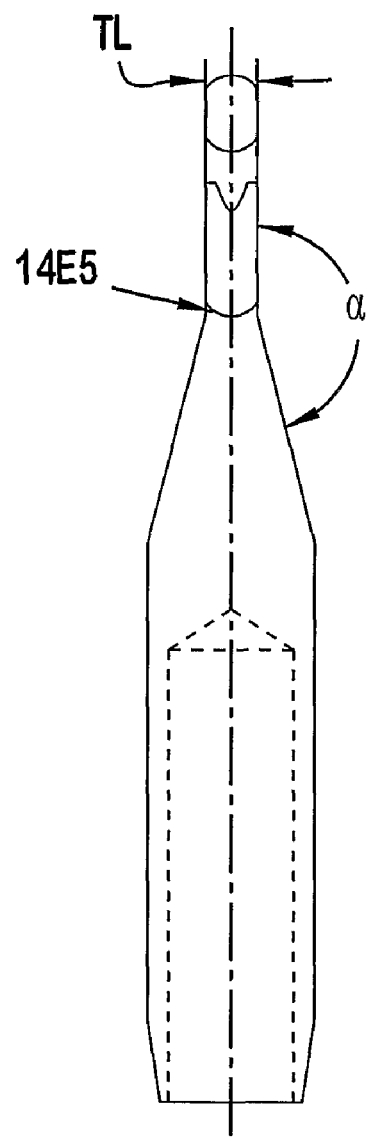
FIG. 9c
FIG. 9d

EMBOLUS BLOOD CLOT FILTER AND DELIVERY SYSTEM

PRIORITY DATA AND INCORPORATION BY REFERENCE

This application is a 35 U.S.C. 371 application of International Application No. PCT/US2006/017890, filed May 9, 2006, which claims priority to U.S. 60/706,596 filed Aug. 9, 2005, the entireties of which are hereby incorporated by reference.

FIELD OF THE INVENTION

This invention relates to a filter device that can be placed via a catheter delivery system in a vessel of a mammalian body to reduce the risk of embolisms. If needed, such filter can be removed from the vessel of a mammalian body without causing traumatic damage to the vessel of a mammalian body.

BACKGROUND OF THE INVENTION

In recent years, a number of medical devices have been designed which are adapted for compression into a small size to facilitate introduction into a vascular passageway and which are subsequently expandable into contact with the walls of the passageway. These devices, among others, include blood clot filters which expand and are held in position by engagement with the inner wall of a vein, such as the vena cava. These vena cava filters are generally designed to remain in place permanently. Such filters include structure to anchor the filter in place within the vena cava, such as elongate diverging anchor members with hooked ends that penetrate the vessel wall and positively prevent migration in either direction longitudinally of the vessel. The hooks on filters of this type are rigid, and within two to six weeks after a filter of this type has been implanted, the endothelium layer grows over the diverging anchor members and positively locks the hooks in place. Now any attempt to remove the filter results in a risk of injury to or rupture of the vena cava.

A number of medical procedures subject the patient to a short term risk of pulmonary embolism which can be alleviated by a filter implant. In such cases, patients are often averse to receiving a permanent implant, for the risk of pulmonary embolism may disappear after a period of several weeks or months. However, most existing filters are not easily or safely removable after they have remained in place for more than two weeks, and consequently longer-term temporary filters that do not result in the likelihood of injury to the vessel wall upon removal are not available.

One potential problem with the known delivery device is that the filter (including the elongated pusher on which the filter is attached thereon) can be pulled backward (i.e., proximally) towards the user, which may result in the inadvertent separation of the pusher assembly and the filter within the delivery device.

Another potential problem that can arise during delivery of a filter results from the placement of various hooks in a delivery device which can lead to the hooks entangling or interfering with one another.

SUMMARY OF THE INVENTION

The various embodiments provide for a blood filter delivery system that resolves potential problems of the known delivery system and filter. The system includes at least in part a catheter introducer, a storage member, an elongated assembly, and a blood filter. The catheter introducer has a coupling port connected to an elongated generally tubular member. The storage member can be coupled to the coupling port of the introducer and an adaptor, a Y-adaptor such as a Touhy-Borst Adapter. The elongated assembly provides a pusher assembly that has a first end that can be disposed in the storage member and a second end extending out of the Touhy-Borst Adapter. The elongated assembly can include a handle, a pusher, a spline member, and the blood filter. The handle can be disposed along a longitudinal axis of the elongated assembly proximate the second end. The pusher is disposed along the longitudinal axis proximate the first end of the elongated assembly. The spline member can be disposed on the elongated assembly along the longitudinal axis between the handle and the pusher. The spline member can have first and second boss portions spaced apart along the longitudinal axis to provide a circumferential gap or space therebetween. Alternatively, the spline member can have a single boss portion with splines and grooves. In an assembled, pre-delivery configuration, a blood filter, which has a plurality of anchor members disposed about the longitudinal axis each having a hook on their ends, is positioned between the pusher and the gap. Each anchor member is positioned within a spline on the first boss portion of the spline member, with an anchor portion disposed in the groove of the spline member.

In yet another aspect, the various embodiments also include a pusher assembly that can be utilized with a vena cava filter delivery unit. The pusher assembly includes an elongated member, a handle, a pusher and a spline member. The elongated member extends along a longitudinal axis from a first end to a second end. The elongated member has a plurality of different cross-sections at various locations along the elongated member. The handle is disposed proximate the first end. The pusher is disposed proximate the second end. The member is disposed along the longitudinal axis between the handle and the pusher. The member has a main body, and first and second boss portions spaced apart along the longitudinal axis to provide a circumferential gap disposed about the longitudinal axis configured so that the gap accommodates a hook of a blood filter. Preferably, the member can be a spline member. Alternatively, the spline member can have a single boss portion with splines and grooves.

In yet a further aspect of the various embodiments, a method of delivering a blood filter is provided. The blood filter has a plurality of anchors about a longitudinal axis. Each of the anchors has a hook and at least two of the anchors define a span intersecting the longitudinal axis. The method can be achieved by locating a curved portion of each hook in an circumferential gap of a support assembly, the gap being disposed between two boss portions of the support assembly; locating a portion of each anchor in a longitudinal groove or spline that extends through one of the two boss portions; and enclosing the filter, including the plurality of locators and hooks, and the boss portions in a generally tubular member having an outside diameter of less than about 10 French (about 3.3 millimeters). Alternatively, the spline member can have a single boss portion with splines and the method can be achieved by positioning an anchor member within a spline in the boss and locating the curved portion of each hook proximal to the boss.

In yet a further aspect of the various embodiments, a bioactive agent can be coupled to the blood filter delivery system or push rod assembly described here. Alternatively, a bioactive agent may be delivered by the blood filter delivery system.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention.

FIGS. 1, 2A, 3A, 4, 5A, and 6A illustrate the components of one embodiment of a blood filter delivery system.

FIGS. 2B and 2C illustrate a proximal portion of a catheter introducer illustrated in FIG. 2A.

FIGS. 3B, 3C, and 3D illustrate various portions of a catheter dilator illustrated in FIG. 3A.

FIG. 4 is a cross sectional perspective view of Touhy-Borst Adapter.

FIGS. 5A and 5B illustrate a filter storage tube.

FIG. 6A illustrates an embodiment of an elongated push wire assembly.

FIGS. 9A, 9B, 9C and 9D illustrate components of respective blood filters usable with the delivery system of FIGS. 1, 2A, 3A, 4, 5A, and 6A.

DETAILED DESCRIPTION OF THE PREFERRED EMBODIMENTS

The various embodiments will be described in detail with reference to the accompanying drawings. Wherever possible, the same reference numbers will be used throughout the drawings to refer to the same or like parts.

As used herein, the terms "about" or "approximately" for any numerical values or ranges indicates a suitable dimensional tolerance that allows the part or collection of components to function for its intended purpose as described herein. Also, as used herein, the terms "patient", "host" and "subject" refer to any human or animal subject and are not intended to be limit the systems or methods to human use, although use of the subject invention in a human patient represents a preferred embodiment.

The blood filter delivery system in the various embodiments mechanically integrates components to safely and reliably deliver and emplace a blood filter, like that illustrated in FIG. 9A, within a patient's blood vessel, such as the inferior vena cava. The system connects with a filter prepackaged in a filter storage tube 15 and includes the tools for properly positioning the filter in the vein and then initiating its deployment in a reliable fashion. Portions of the system may be prepackaged with the filter in the filter storage tube 15.

Figure 1:
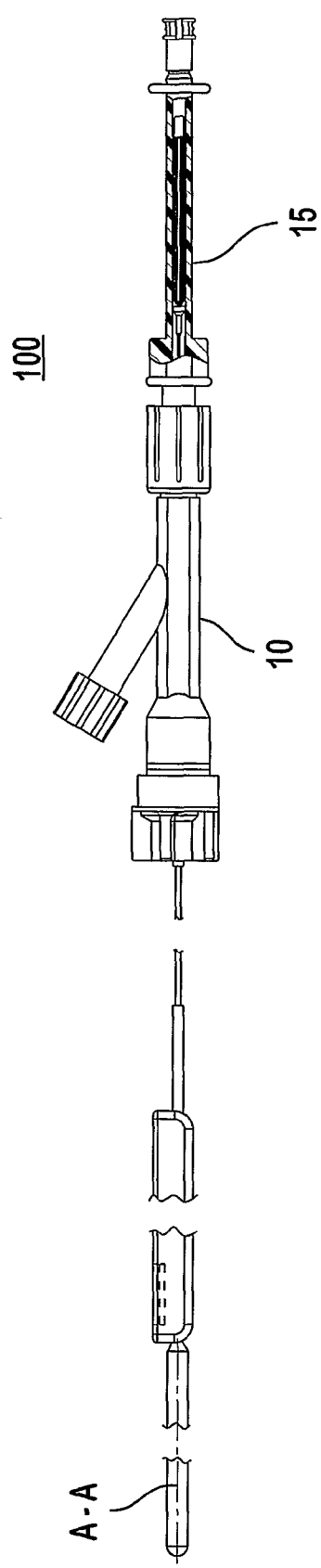

FIGS. 1-11 illustrate one of many exemplary embodiments. In an overview, as shown in FIG. 1, the blood filter delivery system 100 includes a storage tube 15 containing the filter 14, a catheter-like introducer 16 and a pusher assembly 12 to push the filter 14 from the storage tube 15, through the introducer 16 and then into the blood vessel, as well as supporting adapters. The blood filter delivery system 100 for a blood filter device is provided that extends along a longitudinal axis A-A. Components of the system include an adapter, such as a Y-adapter, and in particular a Touhy-Borst Adapter 10 (FIGS. 1 and 4), a filter storage tube 15 (FIGS. 1 and 5A) coupled to the Touhy-Borst Adapter 10 with a filter 14 stored in the storage tube 15 with an elongated pusher assembly 12 (FIG. 6A) that can be used to deploy the filter 14 (FIGS. 9A and 9B) in a blood vessel of a mammal. Other components that can be used with the system include a catheter introducer 16 (FIG. 2A) and a catheter dilator 18 (FIG. 3A). Each of the components in the system 100 is described in further details below.

Figure 2A:
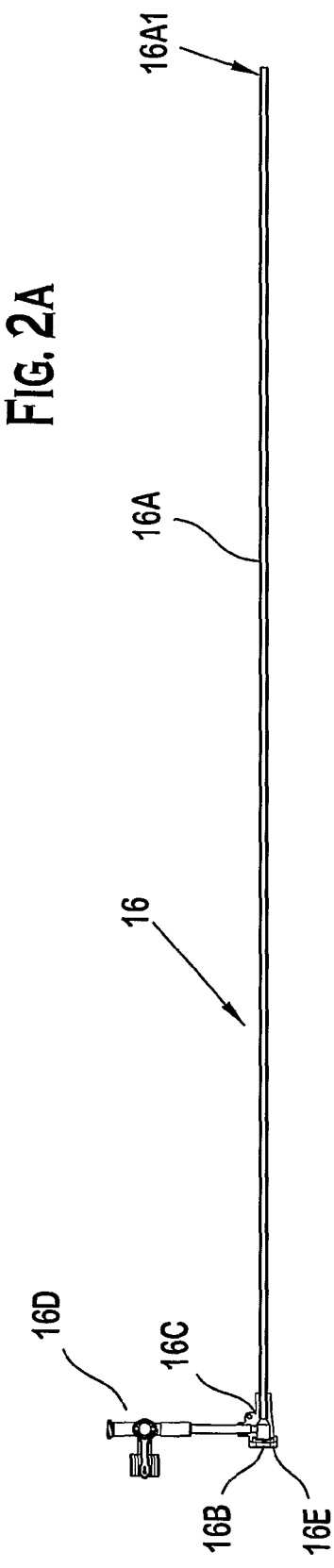
Figure 3C:
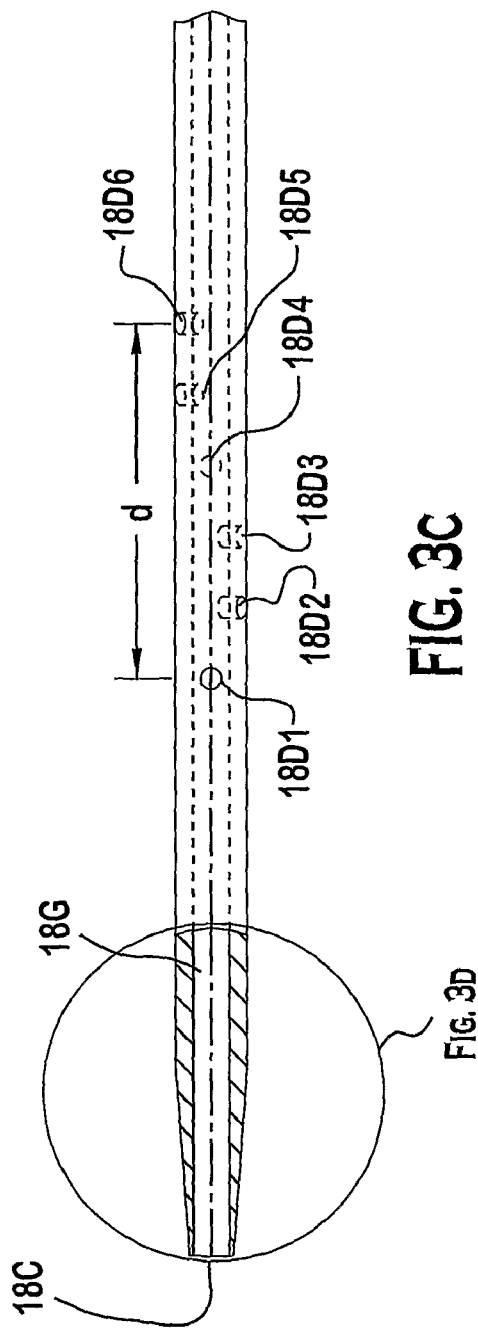
Figure 3D:
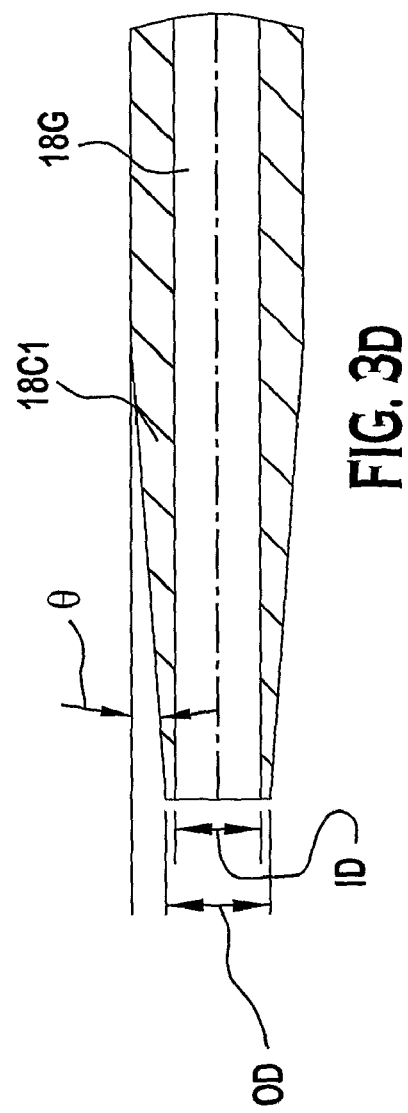

Referring to FIGS. 2A, 2B, and 2C, the catheter introducer 16 includes an elongated generally tubular member, referred to herein as an introducer sheath 16A coupled to a coupling port 16B via an introducer body 16C, which can be provided with a fluid valve 16D. The elongated introducer sheath member 16A is coupled to the introducer body 16C by suitable coupling techniques, such as, but not limited to, for example, threading, bonding, welding, swaging or adhesives. The introducer body 16C can be provided with an internal taper portion 16F that allows for insertion of the external taper portion 15C of the storage tube 15 and to allow for insertion of the filter tip 14E1 or 14E2 without interference by misalignment of the storage tube 15 to the introducer sheath 16A during insertion of the storage tube 15 into the introducer 16. Each of the respective taper portions 16F and 15C is provided with a taper angle of about 10 degrees to about 45 degrees with respect to the longitudinal axis A-A. The introducer sheath member 16A can be formed from a suitable polymer or a combination of polymers and other materials.

In various embodiments, the introducer sheath member 16A can be formed from a range of biocompatible flexible materials, such as polyurethane, polyethylene, polyamide, polyether block amide (PEBA), nylon, and combinations thereof, preferably from a combination of PEBA 70D with a PEBA 55D proximate the tip 16A1. The introducer sheath member 16A can be connected to the introducer body 16C by a bio-compatible adhesive, e.g., cyanoacrylates. In an embodiment, the distal tip 16A1 of the introducer sheath member 16A can be provided with a suitable radio-opaque marker, or include radio-opaque marker substances within the material of the introducer tip 16A1. As used herein, a radio-opaque marker is any material that is identifiable to machine or human readable radiographic equipment while the material is inside a subject's body, such as, by way of example but not by way of limitation, gold, tungsten, platinum, barium sulfate, or tantalum. Preferably, a tantalum radio-opaque marker is formed on or near the tip 16A1 of the introducer sheath 16A.

In a preferred embodiment, the introducer sheath 16A has an outside diameter of less than about 10 French and an inside diameter of less than about 9 French and more preferably, an outside diameter of about 9 French or less and an inside diameter of about 7 French or less, depending upon limits imposed by the diameter of the blood filter in the pre-deployed (i.e., folded) configuration. The introducer sheath 16A can have a length between approximately 305 mm and approximately 920 mm, and most preferably approximately 735 mm.

The introducer body 16C can be provided with a coupling port 16B, which can include a fluid seal 16E interposed between the port opening 16B1 coupled to the introducer sheath member 16A. The fluid seal 16E can be any suitable seal, such as but not limited to, a membrane or a flexible arcuate sectioned seal disposed about a central opening. Preferably, the seal 16E is an elastic membrane made of a suitable biocompatible elastomer, e.g., silicone, with the arcuate sectioned seal disposed about a generally central opening 16B1 for insertion of the dilator 18 or the filter storage tube 15. The introducer body 16C can be coupled to a fluid valve 16D via a polymeric (e.g., PVC) tubing 16F to allow for a suitable fluid (e.g., saline or a bio-active agent including drugs) to be introduced into the introducer sheath 16A or to drain fluid from the introducer member 16A. Preferably, the introducer valve 16D and introducer body 16C are made of polycarbonate, polyethylene, polyurethane, polyamide or PEBA. The coupling port 16B is be provided with an edge 16B2 that can be configured to act in a snap-lock arrangement with a complementary boss portion 18H of the dilator body 18A to attach and retain the dilator body 18A to the introducer body 16C. That is, the coupling port 16B includes the port body 16C that has the port opening 16B1, which has a seal 16E occluding the opening 16B1, and the port body 16C has the edge 16B2 (which may be circumferentially) disposed about the opening 16B1 so as to allow the introducer body 16C to be securable to a projection 15A formed on one end of the storage tube 15 via a sudden sharp engagement. The projection 15A of the storage tube 15 includes a curved surface disposed circumferentially about the longitudinal axis A-A.

During an implantation procedure, a clinician (e.g., surgeon or clinical radiologist) forms an opening to a vessel via a suitable puncture device. Thereafter, a catheter dilator 18 is used in conjunction with the introducer 16 to provide a conduit to the internal of the body so that contrast agent or dye can be provided into the body to determine the implantation site. Referring to FIGS. 3A-3D, the dilator 18 includes a dilator hub 18A coupled to a dilator tube 18B. The dilator body 18A is provided with a threaded fitting 18F at the proximal end to connect to a suitable fluid valve, e.g., the Touhy-Borst Adapter 10 so that fluids can be injected into the dilator fluid passage 18G. A number of fluids can be injected during operation, including dye marker for enabling fluoroscopic imaging of the introducer 16 within the patient, saline to flush body fluids from and provide lubrication within the introducer 16 and, in some embodiments, cooled saline to maintain temperatures of the push wire and/or the filter below their martensitic-to-austenitic transition temperature. The dilator body 18A is coupled to a dilator tube 18B that extends longitudinally to provide a longitudinal passage 18G of approximately 661 millimeters from the dilator body 18A to the distal dilator end 18C. At the distal dilator end 18C, the dilator tube 18B can be provided with a generally truncated conic tip defined by the outer surface of the distal end 18C. The conic tip is utilized to allow the dilator to be inserted through valve 16E and the introducer sheath 16A. The conic tip 18C1 can be defined by a conic outer surface that extends at a conic angle θ of about 4 degrees with respect to the longitudinal axis with an inside diameter ID of about 1 millimeter (about 0.041 inches) and an outside diameter OD of about 2.1 millimeters (about 0.084 inches).

A plurality of fluid communicating ports 18D may be provided through the wall of the dilator tube 18B in a generally spiral configuration to allow for injection of contrasting dye. Each fluid communicating port 18D can be of a suitable configuration such as, but not limited to, for example, circular, square, diamond. Preferably, six circular communicating ports 18D1, 18D2, 18D3, 18D4, 18D5, and 18D6 are provided with an opening diameter of about 0.037 inches, and each port is spaced apart from the adjacent port over a distance d of about 0.16 inches along the longitudinal axis A-A and angularly disposed about the longitudinal axis A-A over an interval of 60 degrees with respect to each adjacent port.

One or more radio-opaque marker band 18E may be coupled to the dilator body 18A by a suitable technique, such as, but not limited to, forming a radio-opaque material integrally with the dilator tube 18B or mounting a separate radio-opaque material onto or inside the dilator tube 18B. Preferably, two radio-opaque markers 18E are swaged onto the dilator tube 18B near the distal end 18C, with a first marker 18E1 located at approximately 28 millimeters from the tip 18C and a second marker 18E2 located at approximately 28 millimeters from the first marker 18E1. In these locations relative to the tip 18C, the radio-opaque markers 18E1 and 18E2 enable a clinician to approximate the inside diameter of a blood vessel under fluoroscopic imaging. In the exemplary embodiments, the ports 18D1-D6 are arranged in a spiral configuration between two radio-opaque marker bands.

Also preferably, the dilator tube 18B can be formed from a variety of biocompatible flexible materials, such as polyurethane, polyethylene, polyamide, polyether block amide (PEBA), nylon, and combinations thereof, preferably from a HDPE/LLDPE blend of polymer and 18-20% of barium sulfate by weight, with the barium sulfate providing the radio-opaque functionality.

When assembled, the dilator tube 1813 slides inside the introducer sheath 16A such that the dilator tube tip 18C1 extends through the introducer tip 16A1. The introducer 16 and catheter dilator 18 can be packaged separately, such as in separate sterilized packages, so they can be unsealed and assembled by the clinician at the time of the procedure. Alternatively, the catheter dilator 18 can be inserted into the introducer 16 at the manufacturer and sealed together in a sterile package, such that the clinician can unpack and use the two components as a unit.

Figure 4:
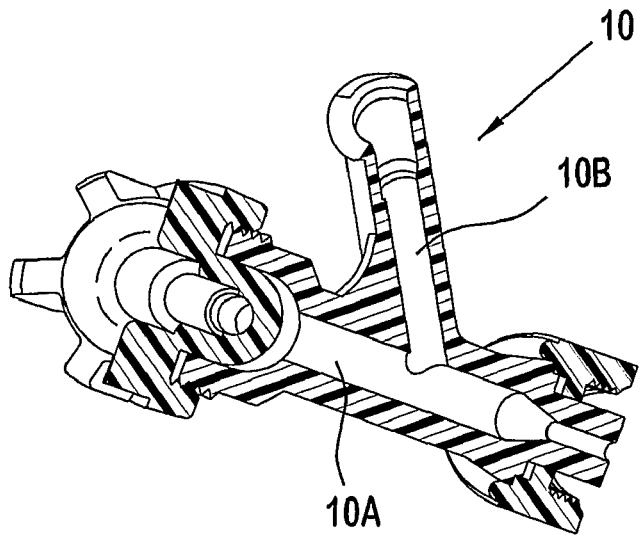

Referring to FIG. 4, the Touhy-Borst Adapter 10 may be provided with at least two passages. A first passage 10A allows for movements of the pusher rod. A second passage 10B allows for flow of saline into the introducer 16 to increase, in most cases, lubricity between the elongated pusher assembly 12 and the introducer 16 as the elongated pusher assembly 12 is moved along longitudinal axis A-A through the second passage 10B and the passage of the introducer 16. The saline solution also can be chilled before introduction into the Touhy-Borst Adapter 10.

Figure 5A:
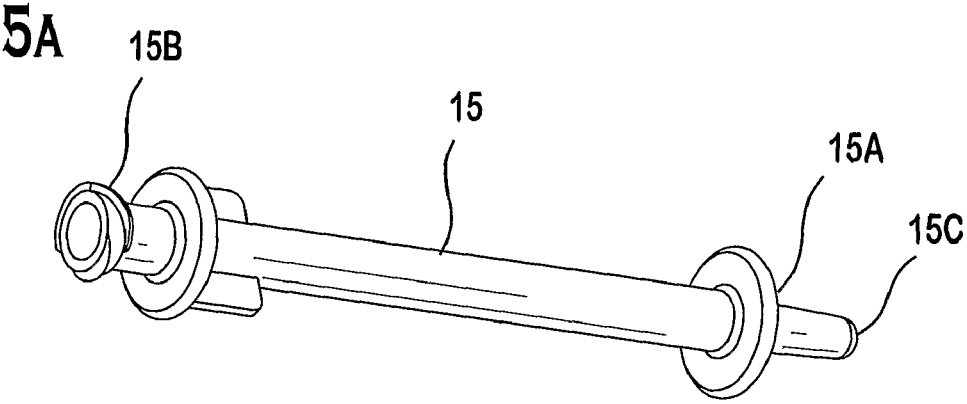
Figure 5B:
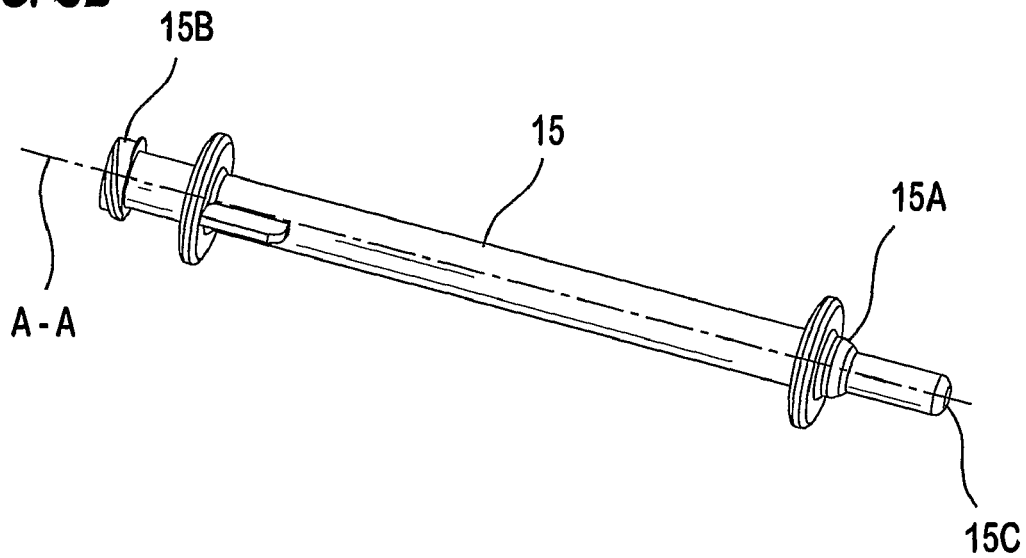

Referring to FIGS. 5A and 5B, a storage tube 15 for various blood filters (e.g., FIGS. 9A and 9B) can be introduced between the Touhy-Borst Adapter 10 and the introducer 16 in the delivery system 100. The storage tube 15 is provided with a suitable fitting (e.g., threaded, snap or luer fitting) at both ends. In the preferred embodiments, the storage tube 15 has a threaded fitting 15B at one end to connect with the Touhy-Borst Adapter 10 and a snap fitting 15A at the other end to connect with the introducer 16, as well as a taper section 15C for insertion into the preferably triple arcuate sectioned elastomeric seal 16E. Alternatively, one end can be provided with a snap-fitting and the other end can be provided with a threaded fitting. The storage tube 15 can be formed from any of a number suitable polymers and, preferably, polycarbonate.

Figure 6A:
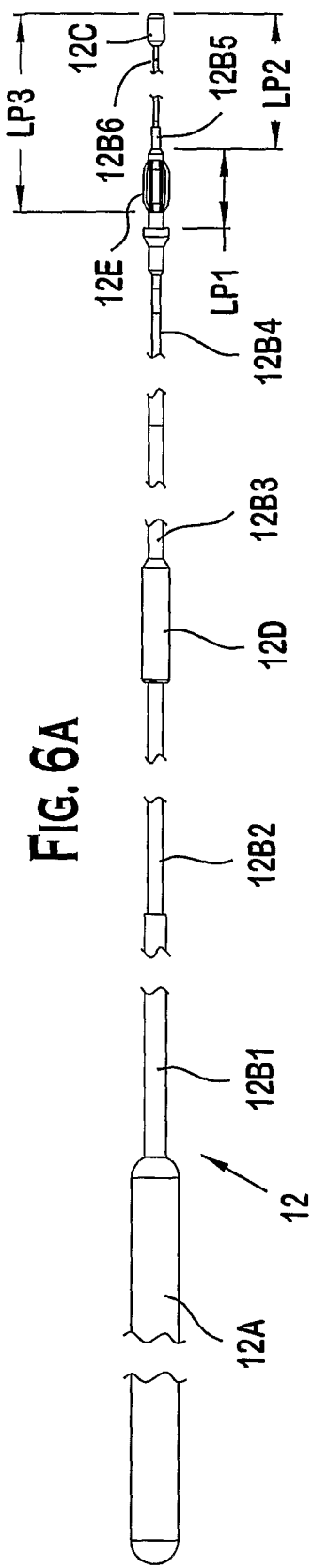

Referring to FIG. 6A, an embodiment of the elongated pusher assembly 12 is shown separate from other components of the delivery system 100. In particular, the pusher assembly 12 can be provided with a handle 12A coupled to an elongated member 12B with various cross-sectional areas 12B11, 12B2, 12B3, 12B4, 12B5, 12B6 and so on at various locations along the pusher assembly 12 from proximate the handle 12A to a pusher 12C. For example, near the handle 12A, the assembly 12 can be provided with a hollow stainless steel tube 12B1 connected to a suitable alloy material, including, for example, a shape memory alloy (e.g., Nitinol), wire on which various members can be disposed thereon such as a stop member or boss portion 12D, spline member 12E and the pusher member 12C. The pusher assembly 12 has a longitudinal length in the range of about 800 mm to about 1000 mm, preferably of about 907 mm. The handle 12A can be formed of a number of metallic, polymer or plastic materials, and is preferably formed from PEBA coupled to a stainless steel hollow section 12B1 having a diameter of about 0.041 inches. The handle 12A is coupled to a super-elastic shape-memory alloy wire having various diameters (e.g., shown at 12B2-12B6) smaller than the diameter of the stainless steel section 12B1 with a diameter at the distal end of about 0.013 inches connected to a generally cylindrical pusher 12C. The utilization of decreasing cross-sectional areas in the pusher assembly allows for flexibility at the distal end and pushability at the proximal end.

The terminal distal end of the generally cylindrical pusher member 12C is longitudinally spaced from a nearest portion of the spline member 12E at a distance of about 34 mm. The pusher member 12C is configured to push against the filter's hub 14D (illustrated in FIG. 8) as the pusher assembly 12 is advanced into the introducer 16. The spline member 12E is configured with a number of radially positioned splines that alternate with grooves in a first portion 12E, each spline being sized to accommodate one of the elongated portions of the anchor members 14B1, 14B2, 14B3, 14B4, 14B5, and 14B6, providing lateral positioning of the anchor member while the filter 14 is in the stored configuration. The pusher member 12C is separated from the spline member 12E by a flexible narrow cross section portion of the pusher wire 12B6 which provides a volume for accommodating both the anchor members 14b and the positioning members 14C of the filter 14. The distal end of the pusher member 12C is separated from the distal end of the spline member 12E by a distance LP2, which is separated from the boss 12E2 by distance LP1. Thus, the overall distance from the distal end of the pusher member 12C to the boss 12E2 of the spline member 12E is distance LP. In other words, LP=LP1+LP2 where LP1 is measured from the planar surface PS to the terminal end 12G and LP2 is measured from the terminal end 12G of the spline member 12E to distal end of the pusher member 12C. To facilitate deployment of the filter 14, the length LP and preferably LP3 is slightly longer than the length LF (FIG. 7A) of the filter 14 in the pre-stored or pre-deployed configuration inside the storage tube 15. This dimensional parameter is believed to impart a lateral force or preload unto the hub of the filter 14. As a consequence, the anchor members are stretched and the push wire portion 12B6 is compressed in the stored configuration. When the filter 14 is deployed and the introducer sheath 16A is retracted proximally sufficient to uncover the hook ends of the anchor members 14A, the anchor members move radially thereby releasing the preload force. Hence, the preload in pusher wire portion 12B6 provides a spring force that helps ensure that the anchoring members are released out of constrainment by the grooves (e.g., 12F1) of the spline member and introducer sheath 16A. The distances LP1, LP2, and LP3 depend upon the dimensions of the filter 14. In an embodiment suitable for use with the filter illustrated in FIGS. 7A, 7B, 9A and 9B, the length LP1 is about 6 millimeters and LP2 is about 34 millimeters so that the total length LP or LP3 is about 40 millimeters.

Figure 6B:
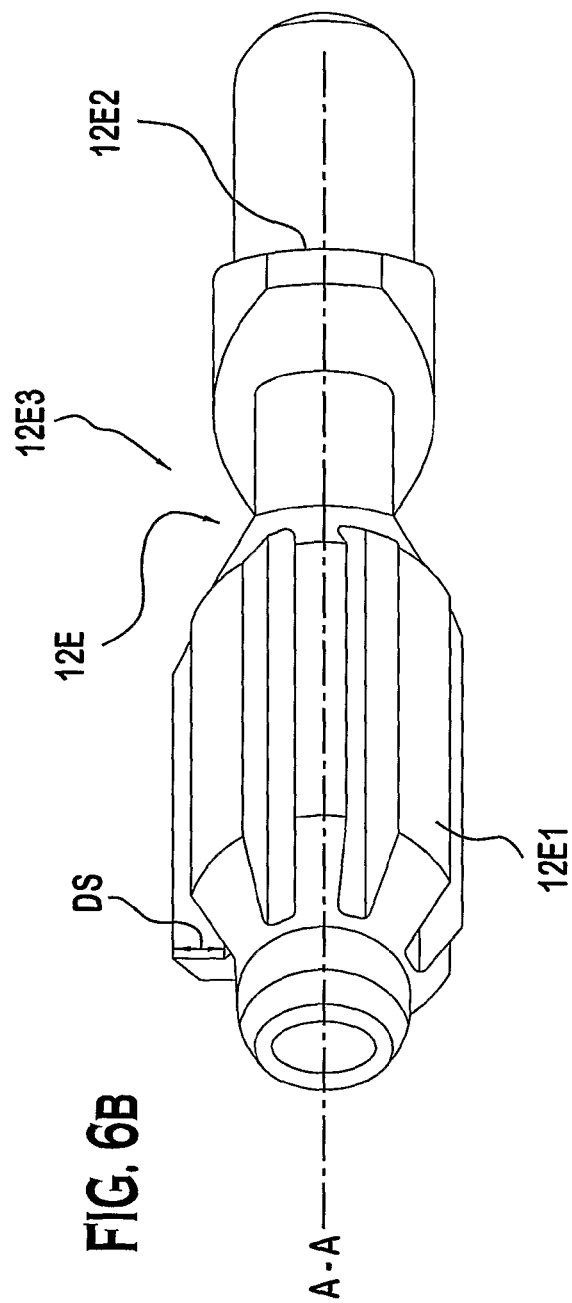
FIGS. 6B and 6C illustrate a splined member of FIG. 6A in two operating configurations.

Referring to FIG. 6B, the spline member 12E has a first boss portion 12E1 and a second boss portion 12E2 spaced apart from each other to define a circumferential gap 12E3 therebetween. The gap 12E3 can be a non-annular gap but preferably is an annular gap in the general shape of a toroid about the longitudinal axis A-A. The first boss 12E1 has a plurality of grooves 12F1-12F6 that extend longitudinally along the longitudinal axis and are disposed, preferably, arcuately about the longitudinal axis through the first boss 12E1. In a preferred embodiment, the longitudinal grooves 12F2 define splines 12SP where each spline extends with a length L of about 3.3 millimeters (about 0.13 inches) along the longitudinal axis at a depth DS of about 0.4 millimeters (about 0.015 inches) radially with respect to the outer surface of the splines 12SP, having a width of about 0.015 inches. Viewed another way, the first boss features a plurality of longitudinal projections (i.e., splines 12SP) spaced apart radially from each other and disposed about a generally cylindrical main surface to define a plurality of longitudinal grooves 12F1-12F6. One longitudinal groove 12F is provided for each anchor member 14B of the blood filter 14. In the assembled and pre-deployment configuration, the anchor members 14B are folded down so that a lower portion lies within a groove 12F as illustrated for one anchor member 14B positioned in groove 12F3 in FIG. 6C. So configured, the grooves 12F hold the anchor members 14B in place, providing lateral stability necessary to prevent anchor members from crossing and becoming entangled during storage and delivery. Similarly, the gap 12E3 provides room for the hook ends of the anchor members to be positioned so as to prevent interference or entanglement, as illustrated in FIG. 7B.

The second boss 12E2 of the spline member 12E can be a generally cylindrical member disposed about the generally cylindrical main surface. As shown in FIG. 6B, a first embodiment of the spline member 12E is provided with a non-circular stop member or second boss portion 12E2. Alternatively, another embodiment of the spline member 12E is provided with a generally circular stop member or boss portion 12E2. In an embodiment, the generally cylindrical boss member includes a generally planar surface PS disposed about the generally cylindrical surface CS and spaced apart from a nearest portion of the first boss 12E1 at a distance G of about 1.3 mm, or about 0.05 inches, along the longitudinal axis. The spline member 12E can be made of a suitable material including, for example, polymers, metal alloys such as Nitinol, titanium, or stainless steel. Preferably, the spline member 12E is made of type-303 stainless steel and processed with appropriate deburring and cleaning operations to render the piece suitable for surgical use.

Figure 6C:
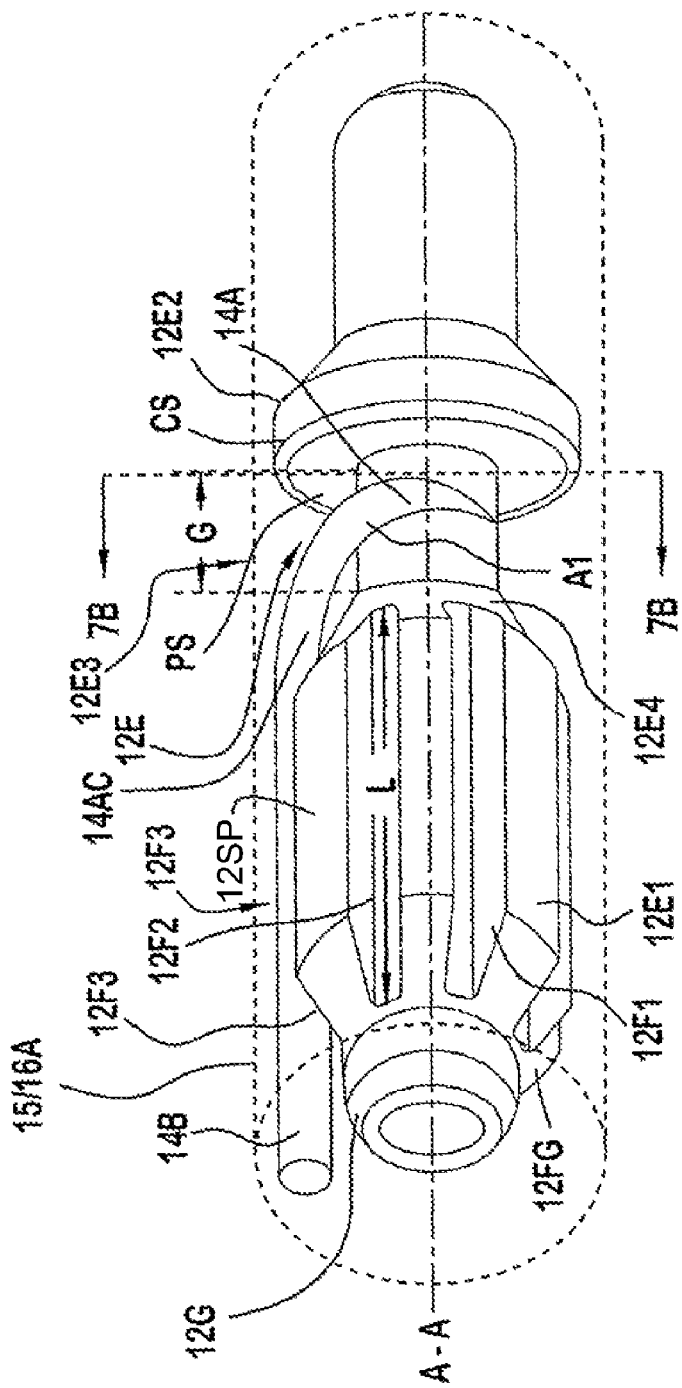

Although the latter embodiment of the spline member 12E in FIG. 6C is preferred, the former embodiment in FIG. 6B having a non-circular stop member or boss portion is believed to allow for the control of the spring force during deployment of the blood filter 14 in some applications of the delivery system 100. Additionally, the non-circular cross section of the second boss 12E2 shown in FIG. 6B permits fluids to pass between the spline member 12E and the walls of the introducer sheath 16A so saline flow can pass through the filter and so the spline member 12E does not function as a piston during insertion and withdrawal movements.

Figure 9B:
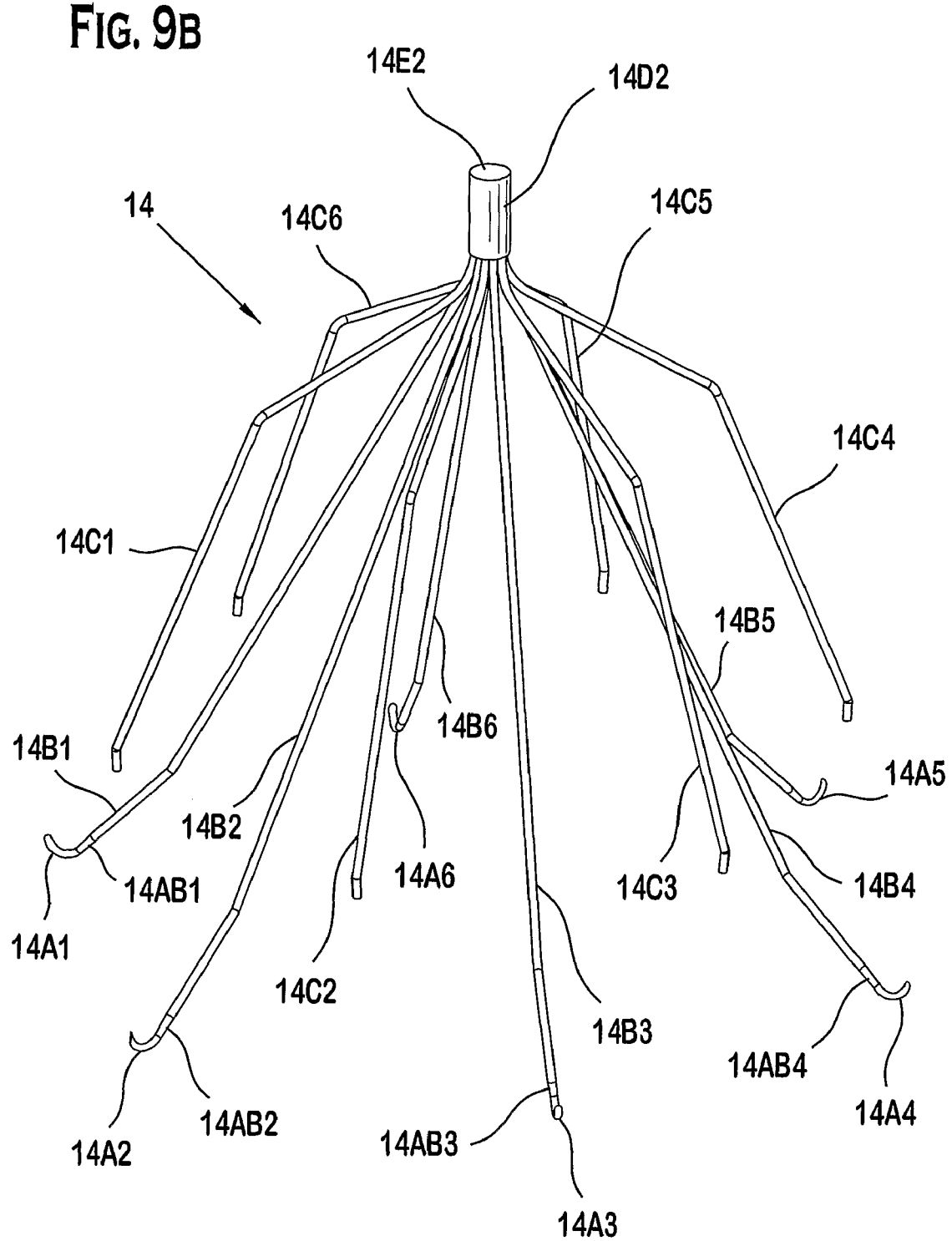

Referring to FIGS. 9A and 9B, two exemplary embodiments of the blood filter 14 are shown. Each filter 14 has some common features. For example, locator members 14C1, 14C2, 14C3, 14C4, 14C5, 14C6 and anchor members 14B11, 14B2, 14B3, 14B4, 14B5, and 14B6 are provided that extend in the same direction from a hub 14D1 or 14D2. Hooks 14A1, 14A2, 14A3, 14A4, 14A5, and 14A6, each having a smaller cross-sectional area than the cross-sectional area of each of the anchor members 14B1-14B6 are respectively connected to the anchor members 14B1-14B6. The spread of the anchor members 14B1-14B6, as measured through the longitudinal axis A-A of the filter 14 or the hub 14D1 or 14D2 is about 40 millimeters in a deployed (but not installed in the blood vessel) position. Differences include the overall length of the two embodiments in which the embodiment of FIG. 9A is about 2 millimeters longer than the embodiment of FIG. 9B in a stored configuration in the storage tube 15; this difference in length being due to the snareable hook on the filter 14 in FIG. 9A. The example blood filters 14 also include a hub 14D1, 14D2 which can serve as the attachment structure for the anchor and locator members. A radio-opaque material can be incorporated in the hub 14D1, 14D2 of the filter. Radio-opaque material can be in the form of an additional structure added to the hub, such as a cap, sleeve, shim, wire or braze included around or in the hub assembly. Alternatively, the hub itself can be formed of a radio-opaque alloy.

Referring to FIGS. 9C and 9D, details of the snareable tip 14E1 for the hub 14D1 are provided. Specifically, the snareable tip 14E1 is believed to allow, optionally, for repositioning (e.g., by capturing and pulling the filter into a catheter) or potentially complete removal of the filter. The snareable tip is provided with a protuberance 14E3 to ensure that a snare will tend to be retained proximate the radiused surface R1. To assist in the capture of a snare (not shown), second radiused surface R2 is included to provide a generally smooth guided entry into the first radiused surface R1. Assisting second radiused surface R2 are tapered side surfaces 14E5 having an included angle α of about 160 degrees. The thickness TL of the tip 14E1 is preferably about 0.5 millimeters (about 0.02 inches), the overall length of the tip and hub is preferably about 7.6 millimeters (about 0.3 inches), and the hub 14D1 is preferably generally circular with an outer diameter of about 1.8 millimeters (about 0.07 inches).

Additional details of the blood filter 14 are provided in provisional patent application Ser. No. 60/680,601 filed on May 12, 2005, which is incorporated by reference in its entirety herein, and as well as in a PCT Patent Application that claims priority to the antecedent provisional patent application, which PCT Patent Application is entitled "Removable Embolus Blood Clot Filter," with PCT Application No. PCT/US06/17889 filed on May 9, 2006, and both applications are hereby incorporated by reference in their entirety.

Figure 10:
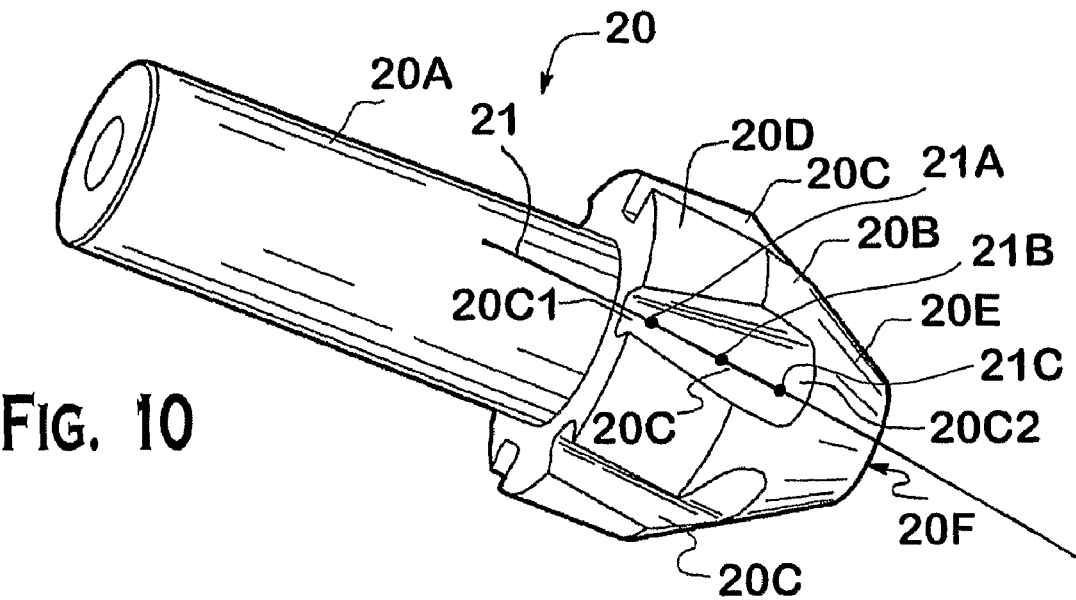
FIG. 10 illustrates an alternative embodiment of the spline member.
Figure 11:
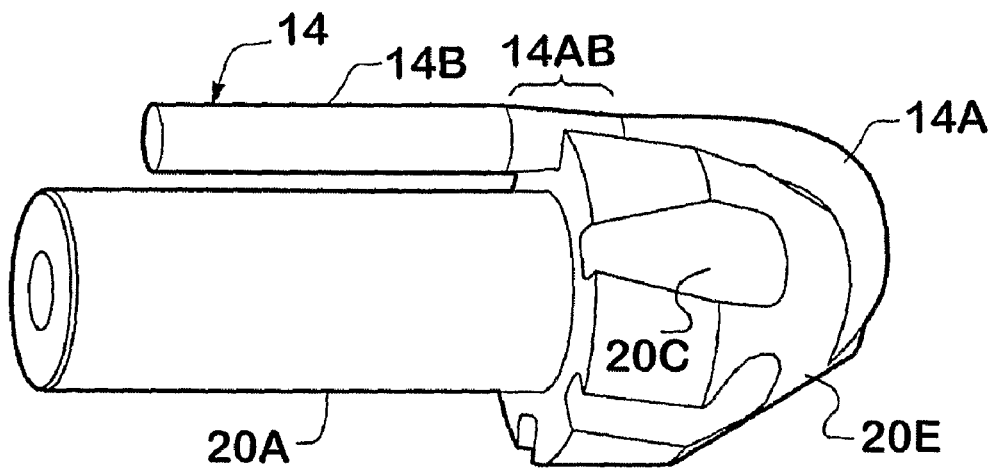
FIG. 11 illustrates a filter anchor member positioned about the spline member illustrated in FIG. 10.

An alternative embodiment for the splined member 20 is illustrated in FIGS. 10 and 11. Referring to FIG. 10, in this embodiment of the splined member 20, the spline portions 20C are provided within the boss 20B. In the embodiment illustrated in FIG. 10, the boss 20B features a first, distal conical surface 20D and a second, proximal conical surface 20E provided before a shaft portion 20A and an end, connector portion 20F. The end portion 20F can include a central bore that may be threaded to accept the distal end of the elongated pusher member 12B4. Grooves 20C provided in the boss 20B are configured to accommodate and radially position the anchor members 14B. In an embodiment illustrated in FIGS. 10 and 11, the grooves 20C are narrower at a distal end 20C1 than at the proximal end 20C2.

Referring to FIG. 11, the conical configuration of portions 20D and 20E are provided so that when the anchor 14 is positioned within the spline 20C, the hook 14A portion fits over the proximal conical portion 20E so that the diameter subtended by the hooks 14A positioned about the boss 20D is less than the interior diameter of the introducer 16. In an embodiment, where the anchors 14 have a narrower width (or cross section) in the hook portion 14A than the shank portion 14B, the narrower distal portion 20C1 of the splines 20D has a groove 20C whose width (as measured on an imaginary outermost circumference connecting the splines 20D) or cross section is smaller than the width or cross section of the anchor shank 14B. In this embodiment, the anchor 14 features a conical shaped portion 14AB where the cross section decreases from that of the shank portion 14B to the hook portion 14A. In other words, at least one anchor portion (e.g., 14B1, 14B2, 14B3, . . . 14B6) of a filter 14 can be located in at least one of the plurality of grooves 20D disposed between splines 20D where the anchor portion (having portions 14A and 14B) has a maximum width at portion 14B greater than a minimum width 20C1 of the groove. Since the narrow portion 20C1 of the spline 20C is wider than the cross section of the hook portion 14A but narrower than the anchor shank portion 14B, the narrow portion 20C1 will engage (e.g., in an interference fit) a portion of the anchor transition portion 14AB. When the anchors 14 are positioned within the grooves 20C in this embodiment, the anchor 14 cannot move in a proximal direction beyond the point where the anchor transition portion 14AB engage the narrow portion 20C1. In this manner, the spline 20C restrains the anchor 14 longitudinally. It should be noted that the narrower portion 20C1 does not have to be located at the proximal end of the boss 20B. Depending on the length of the hook portion 14A, the narrower portion 20C1 can be disposed at any one of a plurality of positions between 21A, 21B, and 21C.

Figure 7A:
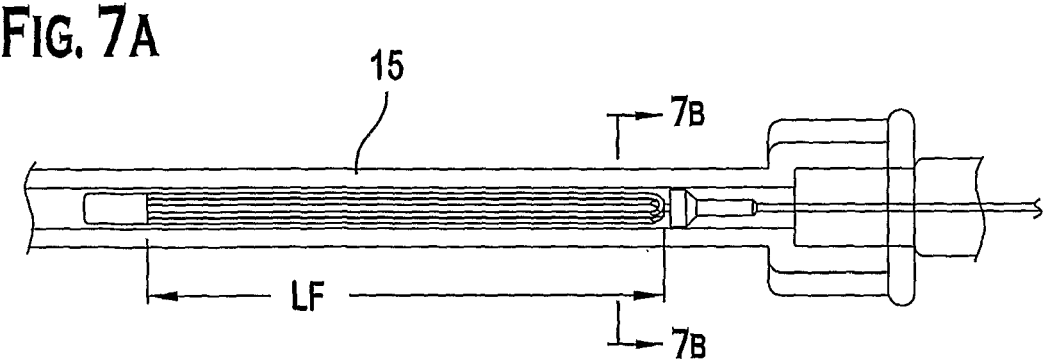
FIGS. 7A and 7B illustrate, respectively, a side view of a filter in a storage tube and coupled to the splined member of FIG. 6B and a sectioned view of the same.
Figure 7B:
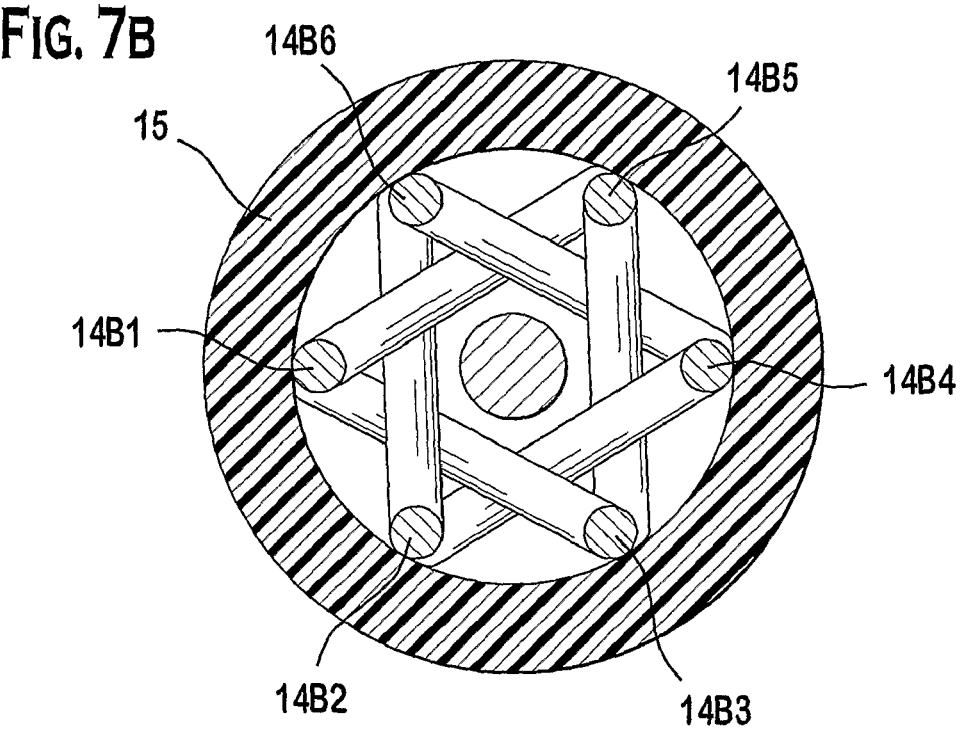

Several design features are believed to be important in advancing the state of the art. For example, the use of the splined member 12E is believed to be important in preventing a pull back of the blood filter 14 from the storage tube 15 toward the proximal direction. Specifically, the spline member 12E is provided with a gap 12E3 to store the hooks of the blood filter 14 in a pre-delivery configuration (FIGS. 6C, 7A, and 7B) that forms an interference fit between the hooks 14AC, the spline member 12E and the storage tube 15 and introducer sheath 16A. For clarity, only one anchor member 14B and hook 14A are shown in FIG. 6C. However, the anchor members 14B1, 14B2, 14B3, 14B4, 14B5, and 14B6 on which the hooks 14A are respectively connected are in a spiral configuration as shown in the side view of FIG. 7A while the hooks are shown in the sectioned-view of FIG. 7B. The placement of the hooks, as shown in the example of FIGS. 6C and 7A, presses the anchor members against the wall of the storage tube 15 and introducer sheath 16A, with the of the hook tip 14B angled in a proximal direction and in contact with the wall as illustrated in FIG. 7B elements 14B1, 14B2, 14B3, 14B4, 14B5, and 14B6. When the filter 14 is advanced in the distal direction, the hook tips 14B slid easily along the wall of the storage tube 15 and introducer sheath 16A. However, if the filter 14 is moved in the proximal direction (towards the right side of FIG. 6C), the tapered surface 12E4 (FIG. 6C) causes a portion of the hook 14A to slide up on the tapered surface 12E4. Because at least the hook 14A is constrained between the spline member and the introducer sheath 16A, a portion of the hook 14A engages one of the wall of the storage tube 15 and introducer sheath 16A in a ratchet-like fashion, presenting a high resistance to motion in that distal direction. As a consequence of this configuration of the filter about the splined member 12E, approximately 5 pound-force is required to cause the filter 14 and pusher assembly 12 to move toward the user or operator (i.e., in a proximal direction) but generally little or no force for movement away from the user or operator (i.e., in a distal direction). That is, the placement of the hooks 14A in relation to the spline member 12E and the storage tube 15/introducer sheath 16A prevents proximal movements of the elongated assembly 12 if the force applied to the assembly 12 is less than a desired value. It should be noted that the desired force value can be selected as being more or less than approximately 5 pound force as a function of at least the cross-sectional area of the hooks 14, the configuration of the spline member 12E (e.g., the angle of tapered surface 12E4), and the inside diameter of the storage tube 15 and introducer sheath 16A. This design feature is believed to prevent inadvertent dislodgement of the anchors from the spline member, which may cause crossing of the anchors.

Additionally, the use of the splined member in the various embodiments described herein is believed to alleviate the problem of the plurality of hooks crossing each other as they are mounted in the storage tube 15 or while the filter is being deployed via the introducer sheath 16A (regardless of whether the filter and system are being tested inside or outside of a host body). In particular, the longitudinal grooves 12F1-12F6 (which can be linear, curved or curvilinear) positioned circumferentially about the longitudinal axis A-A, in combination with the gap 12E3 allows the anchor members 14B and associated hooks 14A to be held in a generally precise configuration (FIG. 7B) while in storage and during delivery into a vein to virtually eliminate the entanglement or crossing of the hooks.

In particular, the use of the splined member 20, shown and described in relation to FIGS. 10 and 11, is believed to reduce a force needed by a clinician to deploy the filter 14 from the distal tip of the introducer during an implantation procedure. The use of spline member 20 reduces an interaction between hooks, sheath wall and marker band to reduce deployment force. Testing has demonstrated the axial force applied to the pusher is approximately 2 lb-force when the spline member 20 (FIG. 10) is utilized.

Further, the use of the complementary snap-fittings for the storage tube 15 and introducer body 16C along with the internal and external tapers 16F and 15C is believed to allow for precise coupling of the two components without having to align the storage tube with the body 16C and threading the two components together, which under some circumstances could result in cross-threading or interference with the tip of the filter 14 into the introducer sheath 16A.

By virtue of the delivery system 100, among other items, described and illustrated herein, a method of packaging a blood filter 14 is provided. As noted above, the filter 14 includes a plurality of anchor members 14B1-14B6 about a longitudinal axis; each of the anchor members 14B1-14B6 having a hook 14A and at least two of the anchor members 14B1-14B6 defining a span intersecting the longitudinal axis and between the at least two anchor members of about 40 millimeters. The method of packaging the filter 14 including hooks 14A having a cross sectional area A1 along the arcuate portion 14AC of the hook 14A that is greater than about 0.04 squared millimeters (or about 0.000057 squared inches), involves locating the curved portion 14AC of each hook in the annular gap 12E3 disposed between the first and second boss portions 12E1 and 12E2 of spline member 12E; and enclosing the filter 14, including the plurality of locators and hooks, and the boss portions in a generally tubular storage tube (e.g., storage tube 15 or introducer sheath 16A) having an outside diameter of less than about 10 French (about 3.3 millimeters) and preferably about 9 French (about 2.9 millimeters) and an inside diameter less than 9 French, preferably less than about 7 French (about 2.3 millimeters). By virtue of the configuration of the blood filter 14 with its hooks 14A, spline member 12E and storage tube 15, the enclosing step further includes preventing movement of the filter 14 relative to the generally tubular member 15 along the longitudinal axis upon application of axial force of less than 5 Pound-force in a proximal direction.

This assembly process for mounting the blood filter on the spline member 12E and loading it into the storage tube 15 is performed prior to shipment to the user or medical practitioner. In an embodiment, the hub 14D of the filter 14 is positioned on the distal end of the pusher member 12C of the pusher assembly 12. The hub is then inserted into the proximal end of the storage tube 15, and as it is advanced the positioning members 14C displaced radially inward to allow the filter 14 to advance into the storage tube 15. Then the anchor members 14A are displaced radially inward as the filter 14 is further advanced into the storage tube 15. As the filter 14 is advanced, the anchor members 14A are positioned one to a groove in the spline portion 12E1 of the spline member 12E, with the hooks 14A1-14A6 fitting into the gap 12E3 in a spiral fashion as illustrated in FIG. 7B. Finally, the filter 14 and pusher assembly 12 are advanced into the storage tube 15 so that the entire spline member 12E is encompassed within the storage tube 15 as illustrated in FIG. 6C. The assembly may further be facilitated by using a jig or other assembly tool to guide the filter members into proper position for loading into the storage tube 15.

To complete assembly, the storage tube 15 can be sealed on both ends to prevent contamination from entering, and the entire assembly of the pusher assembly 12, filter 14 and storage tube 15 sealed in sterile packaging. To avoid kinking of the pusher assembly 12 or lateral forces on the storage tube 15, the entire assembly can be packed in a linear manner within a foam form and hard outer package, such as cardboard or plastic. In a preferred embodiment, the entire assembly is packaged as two separate sterilized units with the introducer and dilator as one sterilized unit and the filter/pusher assembly in a separate sterilized unit.

Figure 6D:
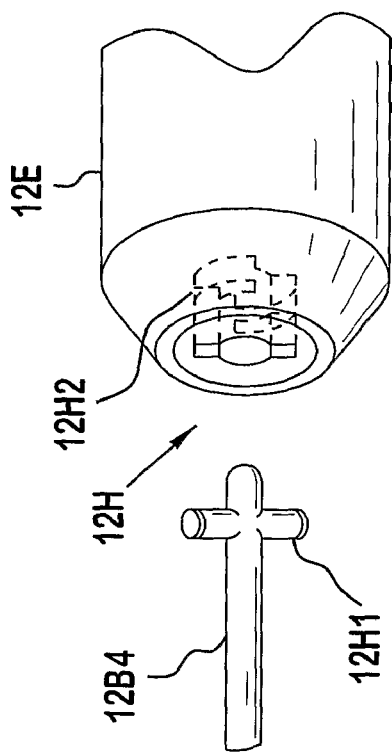
FIGS. 6D, 6E and 6F illustrate embodiments for coupling the spline member illustrated in FIGS. 6B and 6C to the push wire assembly illustrated in FIG. 6A.
Figure 6F:
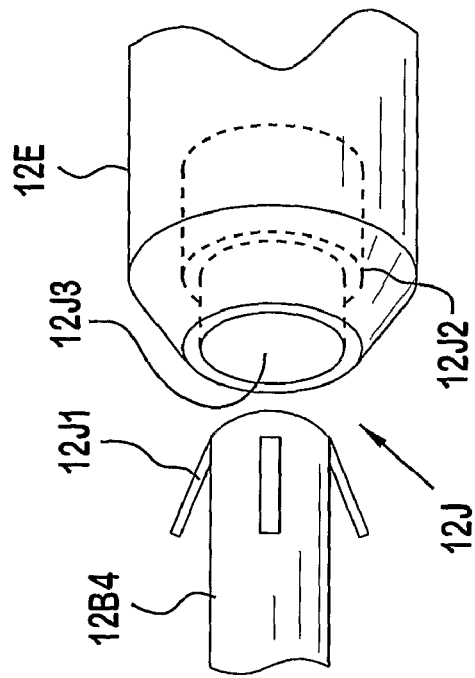
Figure 6E:
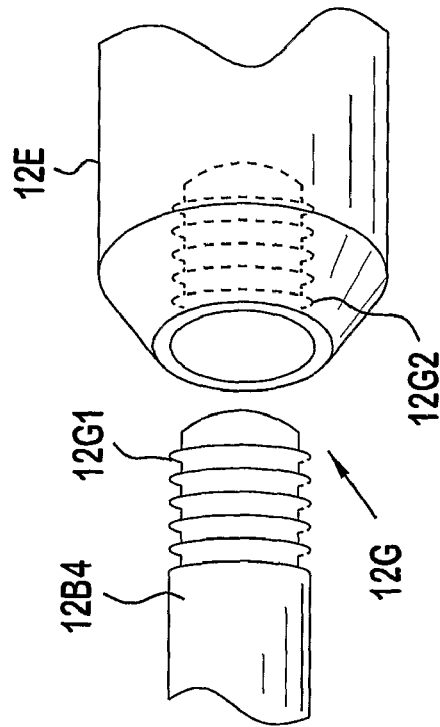

In an alternative embodiment of the pusher assembly, 12, the distal end from the spline member 12E through the pusher member 12C is configured as one piece, and the proximal portions of the pusher assembly, from handle 12A through wire 12B4, configured is one or more pieces, with a coupling mechanism provided for connecting the spline member 12E to the distal end of the push wire 12B4. This embodiment is illustrated in FIGS. 6D, 6E and 6F. As illustrated in these figures, a variety of connection couplings can be used to connect the pusher wire 12B4 to the spline member 12E. By way of example, connector embodiments may include a bayonet connector as illustrated in FIG. 6D, which features a bayonet coupler 16H including tangs 16H1 connected to the push wire 12B4 which engages a bayonet coupling 12H2 within the spline member 12E. Another example; a threaded connection 12G as illustrated in FIG. 6E, which may included a threaded tip 12G1 on the end of the push wire 12B4 which threads into a complementary threaded hole 12G2 in the spline member 12E. A further example is a spring and latch assembly 12J illustrated in FIG. 6 F, that can include spring latches 12J1 mounted on the distal end of the push wire 12B4 which expand into a latching recess 12J2 within the 12E when the distal end of the push wire 12B4 is pushed into the latch opening 12J3. These embodiments permit the filter-spline member/pusher member assembly to placed inside the storage tube 15, such as per the procedure described above, and sealed and stored (such as with caps on each end of the storage tube 15) separate from the long pusher assembly 12A-12B4. Disconnected from the push wire, the filter-spline member-pusher member assembly is less likely to be subjected to lateral forces during shipping, storage and handling. Further, damage to either the push wire 12 or the storage tube 15 does not require the other component to be disposed of. Further, the push wire 12 can be stored in a coiled fashion and uncoiled before assembling to the filter.

In operation for implanting a blood filter into a host, a suitable femoral venous vessel site in the host may be selected. Typically, this is the femoral vein on either the left or right side, depending upon the patient's size or anatomy, the clinician's preference and/or the location of a venous thrombosis. The site can be nicked with a blade and the vein punctured with a suitable entry needle, such as an 18 gage needle, or trocar. A suitable guidewire, such as a J-tipped guidewire, is inserted into the needle and advanced into a distal vena cava or iliac vessel where a filter is to be delivered. Once the guidewire is in position, the entry needle is removed from the patient and slipped off the proximal end of the guide wire. Then the proximal end of the guidewire is inserted into the introducer distal tip 16A1. Saline or a suitable bio-compatible fluid is provided to the introducer valve 16D to remove air in the introducer 16, and then introducer tip 16A1 is inserted into the patient and advanced along the guidewire until it reaches the desired position in the vena cava or iliac vessel. Positioning of the introducer tip 16A1 within the vein at the site for delivering the filter may be confirmed by fluoroscopy, aided by the radio-opaque markers on or within the introducer 16. The dilator tube 18B is then inserted through the introducer body 16C until the dilator hub 18A is snap-fitted onto the coupling port 166B of the introducer 16. Contrasting agent or dye can also be provided to the ports 18D of the dilator tube 18B via the dilator body 18A to provide for visual imaging of the introducer tip 16A1 via suitable fluoroscopic imaging equipment. The guidewire and the dilator 18 can be removed once the user or physician has determined that the introducer tip 16A1 is at the desired location in the vein or vessel.

Saline infusion can be supplied to the Touhy-Borst Adapter 10. The filter 14, which is pre-stored in the storage tube 15, can be coupled to the coupling port 16B via the snap-fitting, and saline can be permitted to flow through the storage tube 15 to provide lubricity between various components of the delivery system 100. The saline may be chilled during portions of the procedure. Similarly, the saline may be warmed during portions of the procedure, such as just prior to releasing the filter into the vein, to help raise the filter and pusher assembly 12 components above the martensitic-to-austenitic transition temperature, causing the filter to seek its annealed shape. The introducer 16, storage tube 15 and elongated pusher assembly 12 are preferably held in a linear configuration to avoid kinking and minimize friction. The filter 14 is physically advanced from the storage tube 15 through the introducer 16 to a position near the distal tip 16A1 of the introducer 16. The advancement of the filter 14 can be accomplished by maintaining the introducer 16 stationary while pushing on the handle 12A of the elongated pusher assembly 12 in the distal direction. The filter 14 is maintained inside the introducer 16, i.e., undeployed at this point. Markings on the pusher assembly 12 may permit the clinician to know the position of the filter 14 with respect to the end of the introducer 16. Additionally, fluoroscopy may be used to track the position of the filter 14 within the introducer 16 and with respect to the patient. When the filter hub 14D approaches the distal end of the introducer 16, the filter is ready to be deployed.

Figure 8:
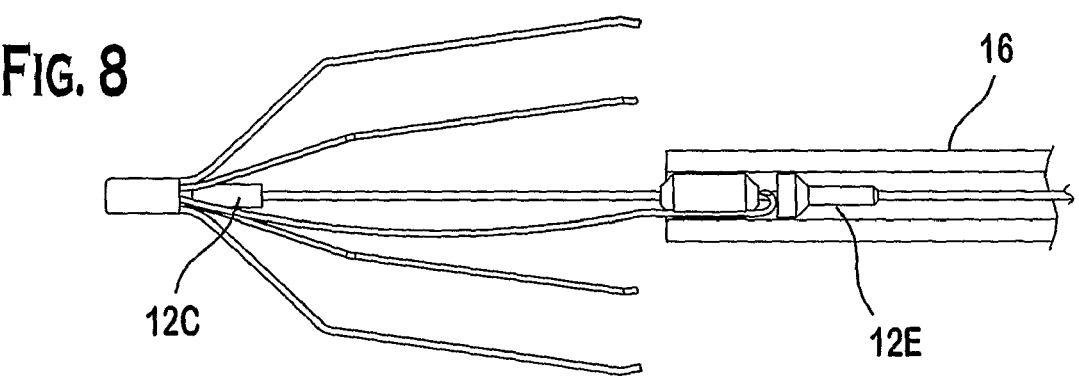
FIG. 8 illustrates the deployment of various locators of a filter as the filter would be deployed in a vessel of a mammalian body.

To deploy the filter 14, the elongated pusher assembly 12 is held stationary while the introducer sheath 16A is pulled back in the proximal direction. This causes the filter to remain in position within the vein, held in place by the pusher member 12C, while the introducer sheath 16A pulls back to release the locator members 14C. Since the locator members 14C are shorter than the anchoring members 14B, the locator members are released first, allowing them to spring out until they contact the walls of the vein. This action places lateral forces on the vein which causes immediate centering of the filter 14 within the vein. A simulation of the deployment of the filter 14 is shown in FIG. 8.

As the introducer 16 is further retracted proximally, the anchor members 14B1-14B6 become unconstrained by the introducer sheath 16A and are free to expand radially. Due to the preload in the push wire portion 12B6 which applies a force through the pusher pad 12C upon the hub of the filter, the filter is released out of the introducer sheath as soon as the hook portions 14A are released from the spline member 12E. Hooks 14A at the ends of the anchor members' 14B1-14B6 begin to dig or penetrate into the blood vessel wall to maintain the filter 14 at approximately the desired location.

Additional information on deployment of this type of filter referenced in the Information for Use is shown and described in U.S. patent application Ser. No. 09/640,865, filed on Aug. 18, 2000, pending, U.S. Pat. Nos. 6,258,026; and 6,007,558. Each of the previously mentioned application and patents is incorporated by reference herein in its entirety into this application.

In another embodiment, bio-active agents can be incorporated with the blood filter or filter delivery system, such as by way of a coating on parts of the filter delivery components (e.g., the pusher pad 12C or the tip of the introducer sheath 16A), or dissolvable structures on, within or attached to the filter delivery components. Alternatively, bio-active agents can be delivered to the region of the filter at the time of the filter emplacement by means of the introducer, either before or after delivery of the filter. Bio-active agent can be included as part of the filter delivery system in order to treat or prevent other conditions (such as infection or inflammation) associated with the filter, or to treat other conditions unrelated to the filter itself. More specifically, bio-active agents may include, but are not limited to:

pharmaceutical agents, such as, for example, anti-proliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine);

antiplatelet agents such as G(GP) IIb/IIIa inhibitors and vitronectin receptor antagonists;

anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), and trazenes-dacarbazinine (DTIC);

anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine});

platinum coordination complexes (cisplatin, carboplatin), procarbazine, hydroxyurea, mitotane, aminoglutethimide;

hormones (i.e. estrogen);

anti-coagulants (heparin, synthetic heparin salts and other inhibitors of thrombin);

fibrinolytic agents (such as tissue plasminogen activator, streptokinase and urokinase), aspirin, dipyridamole, ticlopidine, clopidogrel, abciximab;

antimigratory agents;

antisecretory agents (e.g., breveldin);

anti-inflammatory agents, such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin;

para-aminophenol derivatives i.e. acetominophen;

indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate);

immunosuppressives: (cyclosporine, tacrolimus (FK-506), sirolimus (rapamycin), azathioprine, mycophenolate mofetil);

angiogenic agents, such as vascular endothelial growth factor (VEGF), fibroblast growth factor (FGF);

angiotensin receptor blockers;

nitric oxide donors;

anti-sense oligionucleotides and combinations thereof;

cell cycle inhibitors, such as mTOR inhibitors, and growth factor receptor signal transduction kinase inhibitors;

retenoids;

cyclin/CDK inhibitors;

HMG co-enzyme reductase inhibitors (statins); and protease inhibitors.

While the present invention has been disclosed with reference to certain preferred embodiments, numerous modifications, alterations, and changes to the described embodiments are possible without departing from the sphere and scope of the present invention, which is described, by way of example, in the appended numbered paragraphs below. Accordingly, it is intended that the present invention not be limited to the described embodiments, but that it have the full scope defined by the language of at least the following paragraphs, and equivalents thereof.

What is claimed is:

1. A blood filter delivery system for a blood filter unit, comprising:

an introducer having a coupling port connected to an elongated generally tubular member;

a storage member coupled to the coupling port of the introducer and a Y-adaptor; and a pusher assembly having a distal end disposed in the storage member and a proximal end extending out of the Y-adapter, the pusher assembly including:

a handle disposed along a longitudinal axis of the pusher assembly proximate the proximal end;

a pusher pad disposed along the longitudinal axis of the pusher assembly proximate the distal end;

an elongated member between the handle and the pusher pad, the elongated member having a flexible section with a distal end directly in contact with and continuous with a proximal end of the pusher pad, the flexible section compressed along the longitudinal axis in a predeployed configuration to provide a spring force for filter deployment; and a spline member disposed on the pusher assembly along the longitudinal axis between the handle and the pusher, the spline member having a first boss portion and a second boss portion spaced apart along the longitudinal axis to provide a gap therebetween, the first boss portion including a plurality of longitudinal grooves; and a blood filter having a plurality of anchor members disposed about the longitudinal axis, each of the anchor members having:

a portion disposed in each of the plurality of longitudinal grooves, respectively; and a hook disposed in the gap.

2. The blood filter delivery system according to claim 1, wherein the elongated generally tubular member of the introducer further comprises a radio-opaque marker disposed on the elongated generally tubular member distally with respect to the coupling port.

3. The blood filter delivery system according to claim 2, wherein the coupling port comprises a port body having an opening, the opening including a seal occluding the opening, the port body having an edge disposed about the opening that is securable to a projection formed on one end of the storage member via a sudden sharp engagement.

4. The blood filter delivery system according to claim 3, wherein the projection of the storage member comprises a curved surface disposed circumferentially about the longitudinal axis.

5. The blood filter delivery system according to claim 3, wherein the elongated member comprises a metallic wire having a plurality of differing cross-sections at various locations along the length of the elongated member.

6. The blood filter delivery system according to claim 5, wherein the metallic wire comprises a stainless steel member having a first cross-sectional area connected to a shape memory alloy wire having a second cross-sectional area less than the first cross-sectional area.

7. The blood filter delivery system according to claim 1, wherein the pusher pad comprises a generally cylindrical pusher member disposed proximate the distal end of the elongated assembly, the generally cylindrical pusher member being spaced from a nearest portion of the spline member at a distance of about 34 millimeters.

8. The blood filter delivery system according to claim 7, wherein the first boss portion of the spline member comprises a plurality of longitudinal projections spaced apart from each other and disposed about a generally cylindrical main surface to define the plurality of longitudinal grooves.

9. The blood filter delivery system according to claim 8, wherein the second boss portion of the spline member comprises a generally cylindrical member disposed about the generally cylindrical main surface, the generally cylindrical member having a generally planar surface disposed about the generally cylindrical surface and spaced apart from a nearest portion of the first boss portion at a distance of about 1.3 millimeters along the longitudinal axis.

10. The blood filter delivery system according to claim 1, further comprising a dilator assembly having a dilator hub coupled to an elongated hollow member having a first end proximate the dilator hub and a second end distal to the first end, the second end having a first radio-opaque marker disposed about 28 millimeters from the second end.

11. The blood filter delivery system according to claim 10, wherein the second end comprises a second radio-opaque marker disposed about 28 millimeters from the first radio-opaque marker.

12. The blood filter delivery system according to claim 11, wherein the elongated hollow member comprises a passageway and plurality of fluid ports extending through a wall of the hollow member to the passageway, the plurality of fluid ports being spaced apart from each other in a spiral configuration on the elongated hollow member between the first and second radio-opaque markers.

13. The blood filter delivery system according to claim 1, wherein the filter comprises:

a body extending along a longitudinal axis from a first end to a second end, the body having a snareable tip disposed thereon;

the plurality of anchor members, in an unconstrained configuration of the filter, extending obliquely from the second end of the body away from the longitudinal axis, the plurality of anchor members having a length along the longitudinal axis and defining a maximum width between any two anchor members of at least 0.9 times the length so that each hook connected to each anchor member penetrates a wall of the blood vessel when the filter is placed into the blood vessel;

a plurality of locators, in an unconstrained configuration of the filter, extending obliquely from the second end of the body away from the longitudinal axis so that a portion of each locator engages the wall.

14. The blood filter delivery system according to claim 1, further comprising a bio-active agent.

15. A pusher assembly for use in a vena cava filter delivery unit, the pusher assembly including a filter having a plurality of filter anchor members with a plurality of hooks, the assembly comprising:

an elongated member extending along a longitudinal axis from a proximal end to a distal end, the elongated member having a plurality of cross-sections at various locations along the elongated member, a flexible reduced cross-section disposed at the second end and compressed in a pre-deployed configuration along the longitudinal axis to provide a spring force for filter deployment;

a handle disposed proximate the proximal end of the elongated member;

a pusher pad disposed proximate the distal end of the elongated member, the pusher pad having a proximal end directly in contact with and continuous with a distal end of the flexible reduced cross-section; and a spline member disposed along the longitudinal axis between the handle and the pusher pad, the member having a first boss portion and a second boss portion spaced apart along the longitudinal axis to provide a gap therebetween, the first boss portion including a plurality of longitudinal grooves, wherein each of the grooves accommodates a respective portion of each of the filter anchor members, and wherein the gap accommodates the plurality of hooks.

16. The pusher assembly according to claim 15, wherein the gap comprises an annular gap.

17. The pusher assembly according to claim 15, wherein the elongated member comprises a metallic wire having a plurality of cross-sections at various locations along the length of the elongated member.

18. The pusher assembly according to claim 17, wherein the metallic wire comprises a stainless steel member having a first cross-sectional area connected to a shape memory alloy wire having a second cross-sectional area less than the first cross-sectional area.

19. The pusher assembly according to claim 18, wherein the pusher pad comprises a generally cylindrical pusher member disposed proximate the distal end of the elongated assembly, the generally cylindrical pusher member being spaced from a nearest portion of the spline member at a distance of about 34 millimeters.

20. The pusher assembly according to claim 19, wherein the first boss portion of the member comprises a plurality of longitudinal projections spaced apart from each other and disposed about a generally cylindrical main surface to define the plurality of longitudinal grooves.

21. The pusher assembly according to claim 20, wherein the second boss portion of the member comprises a generally cylindrical member disposed about the generally cylindrical main surface, the generally cylindrical member having a generally planar surface disposed about the generally cylindrical surface and spaced apart from a nearest portion of the first boss portion at a distance of about 1.3 millimeters along the longitudinal axis.

22. The pusher assembly according to claim 15, further comprising a bio-active agent coupled to the pusher assembly proximate the distal end.

23. A pusher assembly for use in a vena cava filter delivery unit, the pusher assembly comprising:

an elongated member extending along a longitudinal axis from a first end to a second end;

a handle disposed proximate the first end;

a pusher disposed proximate the second end;

a spline member disposed along the longitudinal axis between the handle and the pusher, the spline member having a plurality of grooves, each groove defining a plurality of widths along a length thereof; and a filter having a plurality of anchor members terminating in a hook, each anchor member having an anchor portion adjacent to the hook located, respectively, in one of the plurality of grooves, the anchor member having a maximum width greater than a minimum width of the groove, the hook having an end located outside of the groove.

24. The pusher assembly according to claim 23, wherein the plurality of grooves are located in a first conical surface of the spline member.

25. The pusher assembly according to claim 24, wherein each hook is positioned over a second conical surface of the spline member.

26. The pusher assembly according to claim 23, wherein the anchor portion has a frustoconical shape including a first diameter and a second diameter smaller than the first diameter, wherein the first diameter is equivalent to the maximum width of the anchor member.

27. A method of packaging a blood filter having a plurality of anchors about a longitudinal axis, each of the anchors having a hook and at least two of the anchors defining a span intersecting the longitudinal axis and between the at least two anchors of about 40 millimeters, the anchors being coupled to a hub that extends along the longitudinal axis, the method comprising:

positioning a pusher pad connected to a flexible section of an elongate member against the hub;

locating a curved portion of each hook in an annular gap disposed between two boss portions of a support assembly, wherein the support assembly includes a plurality of grooves that extends through one of the two boss portions;

locating a portion of each anchor in each of the longitudinal grooves respectively, such that the flexible section is compressed along the longitudinal axis to provide a spring force for filter deployment; and enclosing the filter, including the plurality of hooks and the boss portions, in a generally tubular member having an outside diameter of less than about 10 French (about 3.3 millimeters in diameter).

28. The method according to claim 27, wherein the locating the curved portion of each hook comprises providing a hook having a cross sectional area along the arcuate portion of the hook greater than 0.04 millimeters squared.

29. The method according to claim 27, wherein the outside diameter is about 9 French (about 2.9 millimeters in diameter).

30. The method according to claim 27, wherein an inside diameter of the generally tubular member is about 7 French (about 2.3 millimeters diameter).

31. The method according to claim 27, wherein the enclosing comprises preventing movement of the filter relative to the generally tubular member along the longitudinal axis upon application of axial force of less than 5 Pound-force in a proximal direction.

32. The method according to claim 27, wherein the enclosing comprises preventing movement of the filter relative to the generally tubular member along the longitudinal axis upon application of axial force of less than 10 Pound-force in a proximal direction.

33. The method according to claim 27, wherein the locating comprises preloading the hub of filter in a distal direction towards an opening of the generally tubular member with the anchors extending in a proximal direction away from the hub.

* * * * *